United States Patent
Simmons

(10) Patent No.: US 11,248,247 B2
(45) Date of Patent: *Feb. 15, 2022

(54) METHODS AND SYSTEMS OF PRODUCING OLIGOSACCHARIDES

(71) Applicant: Cambridge Glycoscience Ltd., Cambs (GB)

(72) Inventor: Thomas Simmons, Cambridge (GB)

(73) Assignee: CAMBRIDGE GLYCOSCIENCE LTD, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/033,321

(22) Filed: Sep. 25, 2020

(65) Prior Publication Data

US 2021/0010043 A1 Jan. 14, 2021

Related U.S. Application Data

(63) Continuation of application No. 16/999,483, filed on Aug. 21, 2020, which is a continuation of application No. PCT/EP2019/054380, filed on Feb. 21, 2019.

(30) Foreign Application Priority Data

Feb. 21, 2018 (EP) .................................. 18157957

(51) Int. Cl.
| | |
|---|---|
| C12P 19/04 | (2006.01) |
| A23L 27/30 | (2016.01) |
| C07H 1/08 | (2006.01) |
| A21D 13/80 | (2017.01) |
| A21D 2/18 | (2006.01) |
| A21D 13/062 | (2017.01) |

(52) U.S. Cl.
CPC .............. *C12P 19/04* (2013.01); *A21D 2/181* (2013.01); *A21D 13/062* (2013.01); *A21D 13/80* (2017.01); *A23L 27/33* (2016.08); *C07H 1/08* (2013.01); *A23V 2002/00* (2013.01); *C12Y 302/01073* (2013.01)

(58) Field of Classification Search
None
See application file for complete search history.

(56) References Cited

U.S. PATENT DOCUMENTS

| | | | |
|---|---|---|---|
| 6,667,066 B2 | 12/2003 | Labeille et al. | |
| 7,033,626 B2 | 4/2006 | Spendler et al. | |
| 7,598,069 B2 | 10/2009 | Felby et al. | |
| 7,754,456 B2 | 7/2010 | Penttila et al. | |
| 7,993,890 B2 | 8/2011 | Soerensen et al. | |
| 8,057,840 B2 | 11/2011 | Harrison et al. | |
| 8,202,842 B2 | 6/2012 | Sinclair et al. | |
| 8,247,200 B2 | 8/2012 | Foody et al. | |
| 8,663,952 B2 | 3/2014 | He et al. | |
| 8,679,794 B2 | 3/2014 | Muniglia et al. | |
| 8,709,763 B2 | 4/2014 | Lali et al. | |
| 8,894,771 B2 | 11/2014 | Floyd et al. | |
| 8,927,038 B2 | 1/2015 | Broekaert et al. | |
| 8,956,846 B2 | 2/2015 | Ben Chaabane et al. | |
| 9,090,916 B2 | 7/2015 | Casanave et al. | |
| 9,113,652 B2 | 8/2015 | Pilling et al. | |
| 9,150,895 B2 | 10/2015 | Kurihara et al. | |
| 9,410,216 B2 | 8/2016 | Eyal et al. | |
| 9,580,729 B2 | 2/2017 | Noda et al. | |
| 9,605,291 B2 | 3/2017 | Yamada et al. | |
| 9,663,836 B2 | 5/2017 | Jansen et al. | |
| 9,670,516 B2 | 6/2017 | Minamino et al. | |
| 9,920,309 B2 | 3/2018 | Reisinger et al. | |
| 9,920,346 B2 | 3/2018 | Funada et al. | |
| 9,955,707 B2 | 5/2018 | Delbaere | |
| 9,963,725 B2 | 5/2018 | Lali et al. | |
| 9,963,728 B2 | 5/2018 | Minamino et al. | |
| 9,982,280 B2 | 5/2018 | Noordam et al. | |
| 10,041,138 B1 | 8/2018 | Eyal et al. | |
| 10,131,923 B2 | 11/2018 | Noordam et al. | |
| 10,167,576 B2 | 1/2019 | Chao et al. | |
| 10,174,351 B2 | 1/2019 | Smits et al. | |

(Continued)

FOREIGN PATENT DOCUMENTS

| | | |
|---|---|---|
| CA | 2831543 A1 | 10/2012 |
| CN | 101899488 A | 12/2010 |

(Continued)

OTHER PUBLICATIONS

Motta et al. A Review of Xylanase Production by the Fermentation of Xylan. Published: May 15, 2013. (Year: 2013).*
Maehara et al. Appl Environ Microbiol. Feb. 15, 2018; 84(4): e01850-17. Published online Jan. 31, 2018. Prepublished online Nov. 27, 2017. (Year: 2017).*
Mathew et al. Applied Microbiology and Biotechnology (2018) 102:3105-3120. Published online Feb. 14, 2018 (Year: 2018).*
Gupta et al. Journal of Environmental Research and Development. vol. 10 No. 03, Jan.-Mar. 2016, pp. 555-563 (Year: 2016).*
Qing et al. Aqueous Pretreatment of Plant Biomass for Biological and Chemical Conversion to Fuels and Chemicals, First Edition. Edited by Charles E. Wyman (2013). Chapter 19, pp. 391-415 (Year: 2013).*
Chica et al. Curr Opin Biotechnol. Aug. 2005;16(4):378-84. (Year: 2005).*

(Continued)

*Primary Examiner* — Christian L Fronda
(74) *Attorney, Agent, or Firm* — Wilson Sonsini Goodrich & Rosati

(57) ABSTRACT

The present invention in the field of oligosaccharide production provides a method of producing oligosaccharides of useful lengths without producing substantial amounts of monosaccharides and disaccharides (illustrated by FIG. 1). There is provided a method for producing an ingredient suitable for incorporation into a foodstuff, cosmetic, or nutraceutical, said ingredient comprising one or more oligosaccharides, wherein the oligosaccharides are produced in an enzymatic reaction, said enzymatic reaction comprising the step of contacting, in a solution or suspension, a polysaccharide-cleaving enzyme and a polysaccharide-containing feedstock, wherein said enzymatic reaction produces substantially no monosaccharides or disaccharides.

27 Claims, 5 Drawing Sheets

Specification includes a Sequence Listing.

(56) References Cited

U.S. PATENT DOCUMENTS

| | | | |
|---|---|---|---|
| 10,253,343 B2 | 4/2019 | Yamada et al. | |
| 10,368,569 B2 | 8/2019 | Toksoz et al. | |
| 10,426,791 B2 | 10/2019 | Speelmans et al. | |
| 10,858,712 B2 | 12/2020 | Kilambi et al. | |
| 11,006,658 B2 | 5/2021 | Simmons | |
| 2003/0091691 A1 | 5/2003 | Olsen et al. | |
| 2007/0248649 A1 | 10/2007 | Sawatzki et al. | |
| 2009/0042266 A1 | 2/2009 | Vehmaanpera et al. | |
| 2009/0062232 A1 | 3/2009 | Fujikawa et al. | |
| 2009/0305935 A1 | 12/2009 | Cascao-Pereira et al. | |
| 2011/0143402 A1 | 6/2011 | De Laat et al. | |
| 2011/0171710 A1 | 7/2011 | Yu et al. | |
| 2012/0035127 A1* | 2/2012 | Goffin | A61P 37/02 514/54 |
| 2012/0115192 A1 | 5/2012 | Lali et al. | |
| 2012/0135500 A1 | 5/2012 | Aehle et al. | |
| 2012/0264873 A1 | 10/2012 | Eyal et al. | |
| 2013/0095531 A1 | 4/2013 | Schooneveld-Bergmans et al. | |
| 2013/0157318 A1 | 6/2013 | Ishikawa et al. | |
| 2013/0164420 A1 | 6/2013 | Catani et al. | |
| 2015/0065454 A1 | 3/2015 | Dupasquier et al. | |
| 2016/0007642 A1 | 1/2016 | Geremia et al. | |
| 2016/0081381 A1 | 3/2016 | Medoff | |
| 2016/0082022 A1 | 3/2016 | Medoff | |
| 2016/0208300 A1 | 7/2016 | Yamada et al. | |
| 2016/0326559 A1 | 11/2016 | Funada et al. | |
| 2016/0340705 A1* | 11/2016 | Lali | C12P 19/04 |
| 2017/0114371 A1 | 4/2017 | Pedersen et al. | |
| 2017/0295805 A1 | 10/2017 | Abu-Hardan et al. | |
| 2017/0303548 A1 | 10/2017 | Krogh et al. | |
| 2017/0303550 A1 | 10/2017 | Abu-Hardan et al. | |
| 2018/0134741 A1 | 5/2018 | Falck | |
| 2019/0029272 A1 | 1/2019 | Niemann | |
| 2019/0153555 A1 | 5/2019 | Eyal et al. | |
| 2019/0233862 A1 | 8/2019 | Cao et al. | |
| 2019/0281874 A1 | 9/2019 | Davidek et al. | |
| 2020/0071736 A1 | 3/2020 | Hammerer et al. | |
| 2020/0123577 A1 | 4/2020 | De Laat et al. | |
| 2020/0263265 A1 | 8/2020 | Wu et al. | |
| 2020/0299791 A1 | 9/2020 | McKay et al. | |

FOREIGN PATENT DOCUMENTS

| | | | |
|---|---|---|---|
| CN | 102925516 A | 2/2013 | |
| CN | 106367449 A | 2/2017 | |
| CN | 107746866 A | 3/2018 | |
| CN | 108157664 A | 6/2018 | |
| CN | 108588144 A | 9/2018 | |
| EP | 1228098 B1 | 9/2006 | |
| EP | 1466926 B1 | 8/2007 | |
| EP | 1751296 B1 | 4/2009 | |
| EP | 1699974 B1 | 7/2009 | |
| EP | 2256208 A1 | 12/2010 | |
| EP | 2235195 B1 | 7/2011 | |
| EP | 2076271 B1 | 9/2011 | |
| EP | 1871400 B1 | 10/2011 | |
| EP | 1811038 B1 | 2/2012 | |
| EP | 2225387 B1 | 9/2012 | |
| EP | 2265127 B1 | 10/2013 | |
| EP | 2665823 A1 | 11/2013 | |
| EP | 2427565 B1 | 1/2014 | |
| EP | 1977652 B1 | 3/2015 | |
| EP | 3010352 A1 | 4/2016 | |
| EP | 3013155 A1 | 5/2016 | |
| EP | 3037005 A1 | 6/2016 | |
| EP | 1706477 B1 | 10/2016 | |
| EP | 2313514 B1 | 11/2016 | |
| EP | 2784156 B1 | 6/2017 | |
| EP | 2996492 B1 | 7/2017 | |
| EP | 3041941 B1 | 12/2017 | |
| EP | 2548966 B1 | 7/2018 | |
| EP | 2548965 B1 | 8/2018 | |
| EP | 3374315 A1 | 9/2018 | |
| EP | 2117322 B1 | 10/2018 | |
| EP | 3177728 B1 | 10/2018 | |
| EP | 3177729 B1 | 10/2018 | |
| EP | 3182830 B1 | 10/2018 | |
| EP | 3190189 B1 | 12/2018 | |
| EP | 3415632 A1 | 12/2018 | |
| EP | 3438272 A1 | 2/2019 | |
| EP | 2917359 B1 | 7/2019 | |
| EP | 3511418 A1 | 7/2019 | |
| EP | 3530743 A1 | 8/2019 | |
| EP | 3541870 A1 | 9/2019 | |
| EP | 2917355 B1 | 10/2019 | |
| EP | 3088530 B1 | 4/2020 | |
| JP | 2006087319 A | 4/2006 | |
| JP | 2008120789 A | 5/2008 | |
| JP | 2009089626 A | 4/2009 | |
| KR | 20190133438 A | 12/2019 | |
| WO | WO-2012133495 A1 | 10/2012 | |
| WO | WO-2013016115 A1 | 1/2013 | |
| WO | WO-2013096603 A2 | 6/2013 | |
| WO | WO-2013159005 A2 | 10/2013 | |
| WO | WO-2014170498 A1 | 10/2014 | |
| WO | WO-2015107413 A1 | 7/2015 | |
| WO | WO-2017057718 A1 | 4/2017 | |
| WO | WO-2018106656 A1 | 6/2018 | |
| WO | WO-2019055717 A1 | 3/2019 | |
| WO | WO-2019102218 A2 | 5/2019 | |
| WO | WO-2019138024 A1 | 7/2019 | |
| WO | WO-2019162416 A1 | 8/2019 | |
| WO | WO-2019227525 A1 | 12/2019 | |
| WO | WO-2019229228 A1 | 12/2019 | |
| WO | WO-2019239366 A1 | 12/2019 | |
| WO | WO-2020009964 A1 | 1/2020 | |
| WO | WO-2020035599 A1 | 2/2020 | |
| WO | WO-2020097458 A1 | 5/2020 | |
| WO | WO-2021032647 A1 | 2/2021 | |
| WO | WO-2021116437 A2 | 6/2021 | |
| WO | WO-2021116437 A3 | 7/2021 | |
| WO | WO-2021140225 A1 | 7/2021 | |

OTHER PUBLICATIONS

Singh et al. Curr Protein Pept Sci. 2017, 18, 1-11 (Year: 2017).*

Basholli-Salihu et al. The Use of Cellobiose and Fructooligosaccharide on Growth and Stability of Bifidobacterium infantis in Fermented Milk. Food and Nutrition Sciences, 2013, 4, 1301-1306. Published Online Dec. 2013. DOI: http://dx.doi.org/10.4236/fns.2013.412167.

Chen et al. Characterization of a novel xylanase from Aspergillus flavus with the unique properties in production of xylooligosaccharides. J Basic Microbiol. Apr. 2019;59(4):351-358. doi: 10.1002/jobm.201800545. Epub Feb. 12, 2019.

Co-pending U.S. Appl. No. 16/844,960, filed Apr. 9, 2020.

Co-pending U.S. Appl. No. 16/999,483, filed Aug. 21, 2020.

Dallabernardina et al. Mixed-Linkage Glucan Oligosaccharides Produced by Automated Glycan Assembly Serve as Tools to Determine the Substrate Specificity of Lichenase. Chemistry. Mar. 2, 2017;23(13):3191-3196. doi: 10.1002/chem.201605479. Epub Feb. 3, 2017.

Danneels et al. A quantitative indicator diagram for lytic polysaccharide monooxygenases reveals the role of aromatic surface residues in HjLPMO9A regioselectivity. PLoS One. 2017; 12(5): e0178446. Published online May 31, 2017. doi: 10.1371/journal.pone.0178446.

Dos Santos et al. Structural basis for xyloglucan specificity and α-d-Xylp(1 → 6)-D-Glcp recognition at the -1 subsite within the GH5 family. Biochemistry. Mar. 17, 2015;54(10):1930-42. doi: 10.1021/acs.biochem.5b00011. Epub Mar. 6, 2015.

El Khoury et al. Beta Glucan: Health Benefits in Obesity and Metabolic Syndrome. J Nutr Metab. 2012; 2012: 851362. Published online Dec. 11, 2011. doi: 10.1155/2012/851362. 28 pages.

EP18157957.4 Extended European Search Report dated Jul. 13, 2018.

Falck et al. Arabinoxylanase from glycoside hydrolase family 5 is a selective enzyme for production of specific arabinoxylooligosac-

(56) References Cited

OTHER PUBLICATIONS charides. Food Chem. Mar. 1, 2018;242:579-584. doi: 10.1016/j.foodchem.2017.09.048. Epub Sep. 12, 2017.
Fanuel et al. The Podospora anserina lytic polysaccharide monooxygenase PaLPMO9H catalyzes oxidative cleavage of diverse plant cell wall matrix glycans. Biotechnol Biofuels. 2017; 10: 63. Published online Mar. 11, 2017. doi: 10.1186/s13068-017-0749-5.
Gorton. Spare the sugar. bakingbusiness.com. Mar. 31, 2013. Retrieved Sep. 16, 2020 from: https://www.bakingbusiness.com/articles/34774-spare-the-sugar. 8 pages.
Goubet et al. Polysaccharide analysis using carbohydrate gel electrophoresis: a method to study plant cell wall polysaccharides and polysaccharide hydrolases. Anal Biochem. Jan. 1, 2002;300(1):53-68.
Kracher et al. Active-site copper reduction promotes substrate binding of fungal lytic polysaccharide monooxygenase and reduces stability. J Biol Chem. Feb. 2, 2018; 293(5): 1676-1687. Published online Dec. 19, 2017. doi: 10.1074/jbc.RA117.000109.
Linares-Pastén et al. Structural Considerations on the Use of Endo-Xylanases for the Production of prebiotic Xylooligosaccharides from Biomass. Curr Protein Pept Sci. Jan. 2018; 19(1): 48-67. Published online Jan. 2018. doi: 10.2174/1389203717666160923155209.
Loose et al. Activation of bacterial lytic polysaccharide monooxygenases with cellobiose dehydrogenase. Protein Sci. Dec. 2016; 25(12): 2175-2186. Published online Sep. 26, 2016. doi: 10.1002/pro.3043.
Meier et al. Oxygen Activation by Cu LPMOs in Recalcitrant Carbohydrate Polysaccharide Conversion to Monomer Sugars. Chem Rev. Mar. 14, 2018; 118(5): 2593-2635. Published online Nov. 20, 2017. doi: 10.1021/acs.chemrev.7b00421.
Nordberg Karlsson et al. Endo-xylanases as tools for production of substituted xylooligosaccharides with prebiotic properties. Appl Microbiol Biotechnol. 2018; 102(21): 9081-9088. Published online Sep. 8, 2018. doi: 10.1007/S00253-018-9343-4.
Park et al. Effect of fructo-oligosaccharide and isomalto-oligosaccharide addition on baking quality of frozen dough. Food Chem. Dec. 15, 2016;213:157-162.doi: 10.1016/j.foodchem.2016.06.067. Epub Jun. 21, 2016.
PCT/EP2019/054380 International Search Report and Written Opinion dated Jun. 27, 2019.
PCT/EP2019/072026 International Search Report and Written Opinion dated Dec. 2, 2019.
Schmiele et al. Mixolab™ for rheological evaluation of wheat flour partially replaced by soy protein hydrolysate and fructooligosaccharides for bread production. LWT—Food Science and Technology, vol. 76, Part B, pp. 259-269 (Mar. 2017). Available online Jul. 5, 2016. DOI: https://doi.org/10.1016/j.lwt.2016.07.014.
Short-Chain Fructooligosaccharides: Handling/Processing. Technical Evaluation Report. U.S. Department of Agriculture (USDA) Agricultural Marketing Service (AMS). Aug. 11, 2006. Retrieved Sep. 16, 2020 from URL: https://www.ams.usda.gov/sites/default/files/media/Fructooligosaccharides%20TR.pdf, 7 pages.
Simmons et al. An unexpectedly lichenase-stable hexasaccharide from cereal, horsetail and lichen mixed-linkage β-glucans (MLGs): implications for MLG subunit distribution. Phytochemistry. Nov. 2013;95:322-32. doi: 10.1016/j.phytochem.2013.08.003. Epub Sep. 8, 2013.
Simmons et al. Bonds broken and formed during the mixed-linkage glucan : xyloglucan endotransglucosylase reaction catalysed by Equisetum hetero-trans-β-glucanase. Biochem J. Apr. 1, 2017; 474(7): 1055-1070.Published online Mar. 8, 2017. Prepublished online Jan. 20, 2017. doi: 10.1042/BCJ20160935.
Simmons et al. Structural and electronic determinants of lytic polysaccharide monooxygenase reactivity on polysaccharide substrates. Nat Commun. 2017; 8: 1064. Published online Oct. 20, 2017. doi: 10.1038/s41467-017-01247-3.
Tanaka et al. Creation of cellobiose and xylooligosaccharides-coutilizing Escherichia coli displaying both β-glucosidase and β-xylosidase on its cell surface. ACS Synth. Biol. 2014, 3, 7, 446-453. Published online Oct. 24, 2013. DOI: https://doi.org/10.1021/sb400070q.
U.S. Appl. No. 16/844,960 Office Action dated Sep. 22, 2020.
Villares et al. Lytic polysaccharide monooxygenases disrupt the cellulose fibers structure. Sci Rep. 2017; 7: 40262. Published online Jan. 10, 2017. doi: 10.1038/srep40262.
Wang et al. Relative fermentation of oligosaccharides from human milk and plants by gut microbes. European Food Research and Technology, vol. 243, pp. 133-146 (2017). Published online Jun. 20, 2016.
Xiao et al. Application of Xylo-oligosaccharide in modifying human intestinal function. African Journal of Microbiology Research 6(9):2116-2119 (Mar. 9, 2012).
Hakala et al. Enzyme-aided alkaline extraction of oligosaccharides and polymeric xylan from hardwood kraft pulp. Carbohydr Polym. Mar. 1, 2013;93(1):102-8.doi: 10.1016/j.carbpol.2012.05.013. Epub May 11, 2012.
Qi et al. Application of ultrafiltration and nanofiltration for recycling cellulase and concentrating glucose from enzymatic hydrolyzate of steam exploded wheat straw. Bioresour Technol. Jan. 2012;104:466-72. doi: 10.1016/j.biortech.2011.10.049. Epub Oct. 31, 2011.
Zhang et al. Hemicellulose isolation, characterization, and the production of xylo-oligosaccharides from the wastewater of a viscose fiber mill. Carbohydr Polym. May 5, 2016;141:238-43.doi: 10.1016/j.carbpol.2016.01.022. Epub Jan. 12, 2016.
Beldman et al. Application of cellulase and pectinase from fungal origin for the liquefaction and saccharification of biomass. Enzyme and Microbial Technology, vol. 6, Issue 11, pp. 503-507 (Nov. 1984). DOI: https://doi.org/10.1016/0141-0229(84)90004-8.
Hang et al. Enzymatic Production of Soluble Sugars from Corn Husks. LWT—Food Science and Technology, vol. 32, Issue 4, pp. 208-210 (Jun. 1999). DOI: https://doi.org/10.1006/fstl.1998.0530.
Sun et al. Hydrolysis of lignocellulosic materials for ethanol production: a review. Bioresour Technol. May 2002;83(1):1-11. doi: 10.1016/s0960-8524(01)00212-7.
Watanabe, Eiichi. Membrane Separation in Cellulose Saccharification and Mixed Enzyme Culture Liquid Recycling. [Medicine and Biology, vol. No. 119, Issue No. 3, Sep. 10, 1989]. 7 pages.
Brijwani et al. Production of a cellulolytic enzyme system in mixed-culture solid-state fermentation of soybean hulls supplemented with wheat bran. Process Biochemistry, vol. 45, No. 1, 120-128 (2010).
Co-pending U.S. Appl. No. 17/229,628, inventor Simmons; Thomas J., filed Apr. 13, 2021.
De La Fuente et al. Development of a robust method for the quantitative determination of disaccharides in honey by gas chromatography. J Chromatogr A, 1135 (2006) 212-218.
Greek Yogurt with Honey Base, Database Accession No. 4046243, Database GNPD online (Jun. 6, 2016). Mintel. 4 pages.
Jayapal et al. Value addition to sugarcane bagasse: Xylan extraction and its process optimization for xylooligosaccharides production. Industrial Crops and Products, vol. 42, pp. 14-24 (2013).
Karadeniz et al. Sugar composition of apple juices. European Food Research and Technology, vol. 215, pp. 145-148 (2002).
Kuhad et al. Microbial Cellulases and Their Industrial Applications. Enzyme Res. 2011; 2011: 280696. Published online Sep. 7, 2011. doi: 10.4061/2011/280696.
Lecumberri et al. A diet rich in dietary fiber from cocoa improves lipid profile and reduces malondialdehyde in hypercholesterolemic rats. Nutrition.Apr. 2007;23(4):332-41.doi: 10.1016/j.nut.2007.01.013. Epub Mar. 23, 2007.
PCT/EP2021/050311 International Search Report and Written Opinion dated May 3, 2021.
U.S. Appl. No. 16/844,960 Notice of Allowance dated Feb. 3, 2021.
U.S. Appl. No. 17/083,121 Office Action dated May 14, 2021.
PCT/EP2020/085810 International Search Report and Written Opinion dated Jun. 9, 2021.
U.S. Appl. No. 17/083,121 Notice of Allowance dated Aug. 23, 2021.
Co-pending U.S. Appl. No. 17/083,121, inventor Simmons; Thomas J., filed Oct. 28, 2020.

(56) References Cited

OTHER PUBLICATIONS

EFSA Panel on Dietetic Products, Nutrition and Allergies (NDA) (2018). Safety of xylo-oligosaccharides (XOS) as a novel food pursuant to Regulation (EU) 2015/2283: (Scientific Opinion). E F S A Journal, 16(7), [5361], DOI: https://doi.org/10.2903/j.efsa.2018.5361. 20 pages.

GRAS Notification—Claim of GRAS Status (Revised May 21, 2010), Claim of Exemption from the Requirement for Premarket Approval Requirements Pursuant to Proposed 21 CFR § 170.36(c)(1), p. 000007 and 000015. EAS Consulting Group, LLC, Alexandria, Virginia, USA. Retrieved Dec. 2 from URL: http://wayback.archive-it.org/7993/20171031045331/https://www.fda.gov/downloads/Food/IngredientsPackagingLabeling/GRAS/NoticeInventory/UCM269544.pdf.

PCT/EP2020/072929 International Search Report and Written Opinion dated Dec. 8, 2020.

* cited by examiner

METHODS AND SYSTEMS OF PRODUCING OLIGOSACCHARIDES

CROSS-REFERENCE

This application is a continuation application of U.S. application Ser. No. 16/999,483, filed Aug. 21, 2020, which is a continuation of International Application Serial No. PCT/EP2019/054380, filed Feb. 21, 2019, which claims priority to European Application Serial No. 18157957.4, filed Feb. 21, 2018, all of which each application is incorporated by referenced in their entirety.

SEQUENCE LISTING

The instant application contains a Sequence Listing which has been submitted in ASCII format via EFS-Web and is hereby incorporated by reference in its entirety. Said ASCII copy, created on Sep. 23, 2020, is named 56406_704_302_ST25.txt and is 41.6 kilobytes in size.

FIELD OF THE INVENTION

The invention relates to the enzymatic production of oligosaccharides and their use in foodstuffs, cosmetics, and nutraceuticals.

BACKGROUND OF THE INVENTION

Sugary foods and drinks are an important part of culture and lifestyle habits across the world, but the sugar they contain has been linked to obesity, diabetes, poor dental health, and disruptive behaviour in people. Because of this, consumer preferences have been shifting away from sugar-containing foods, and governments are increasingly implementing regulation to encourage the consumption of less sugar.

As such, industry has been searching for appropriate low-calorie sweeteners for many decades to substitute for sugar in food and beverages. Unfortunately, many sugar substitutes are produced from non-natural resources, and often offer bitter undertones or other unpleasant tastes along with their sweetness, both of which consumers find unappealing. Moreover, while sweeteners are able to mimic the sweetness of sugar in food and drinks, few are able to mimic the other aspects of sugar such as adding bulk, modulating texture, providing structure, acting as a preservative, and modulating colour and flavour through caramelisation and Maillard reactions.

Dietary fibre is an important part of a positive diet, and helps maintain digestive health and a well-regulated gut flora. Such fibre comprises polysaccharides of varying chain lengths and saccharide types. In addition to being found naturally in a wide spectrum of foods, fibre can also be produced separately and added to other foods during their manufacture.

Methods of industrially producing dietary oligosaccharides may involve chemically or enzymatically cleaving long polysaccharides into shorter chains. However, in addition to chains of the desired length, mono- and di-saccharides are liberated by this cleaving action. Because mono- and di-saccharides are classed as 'sugar' in nutritional labelling, and because they cause the negative effects on human health described above, they are undesirable in many food uses for oligosaccharides. Glucose, galactose, fructose, maltose, sucrose and lactose in particular are undesired, as they are calorific. However, despite the negative associations with excess mono- and di-saccharides on human health, compositions comprising high levels of mono- and di-saccharides, such as 100%, are abundantly used in the food industry.

SUMMARY OF THE INVENTION

The present inventor has found that sugar compositions comprising longer chained saccharides (oligosaccharides), which replace substantial amounts of the mono- and di-saccharides in the presently used compositions, still provide the desired sweetness and texture properties in a foodstuff. However, the negative effects that are associated with the current sugar compositions on human health are significantly improved; for example, the compositions of the present invention contain far fewer calories and have less impact on dental health.

Furthermore, the present inventor has discovered enzymatic methods of producing oligosaccharides of useful lengths without producing substantial amounts of monosaccharides and disaccharides, and has found that foodstuffs derived from these oligosaccharides have improved characteristics. Monosaccharides and disaccharides are often removed from oligosaccharide compositions, adding time, complexity, energy, and expense to the manufacturing process. As a result, the inventor's novel methods are useful in manufacturing foodstuffs, nutraceuticals, and cosmetic products.

Further, the inventor has found that when the enzyme is a Lytic Polysaccharide Monooxygenase (LPMO), some of the oligosaccharide chains produced have chemical modifications at one or both termini which may modulate the flavour, colour, caramelisation, and other properties of the oligosaccharide in such ways as are useful in the food industry.

According to a first aspect of the invention, there is provided a method for producing an ingredient suitable for incorporation into a foodstuff, cosmetic, or nutraceutical, said ingredient comprising one or more oligosaccharides, wherein the oligosaccharides are produced in an enzymatic reaction, said enzymatic reaction comprising the step of contacting, in a solution or suspension, a polysaccharide-cleaving enzyme and a polysaccharide-containing feedstock, wherein said enzymatic reaction produces substantially no monosaccharides or disaccharides.

According to a second aspect of the invention, there is provided an ingredient for incorporation into a foodstuff, cosmetic, or nutraceutical, comprising β-1,4-glucan oligosaccharides, wherein one or more terminal saccharide residues are oxidised to a lactone, a 4-ketoaldose, an aldonic acid or a geminal diol, and wherein the ingredient comprises substantially no monosaccharides or disaccharides.

According to a third aspect of the invention, there is provided an ingredient for incorporation into a foodstuff, cosmetic, or nutraceutical, comprising β-1,4-glucan oligosaccharides and another oligosaccharide.

DETAILED DESCRIPTION OF THE INVENTION

Figure 1:
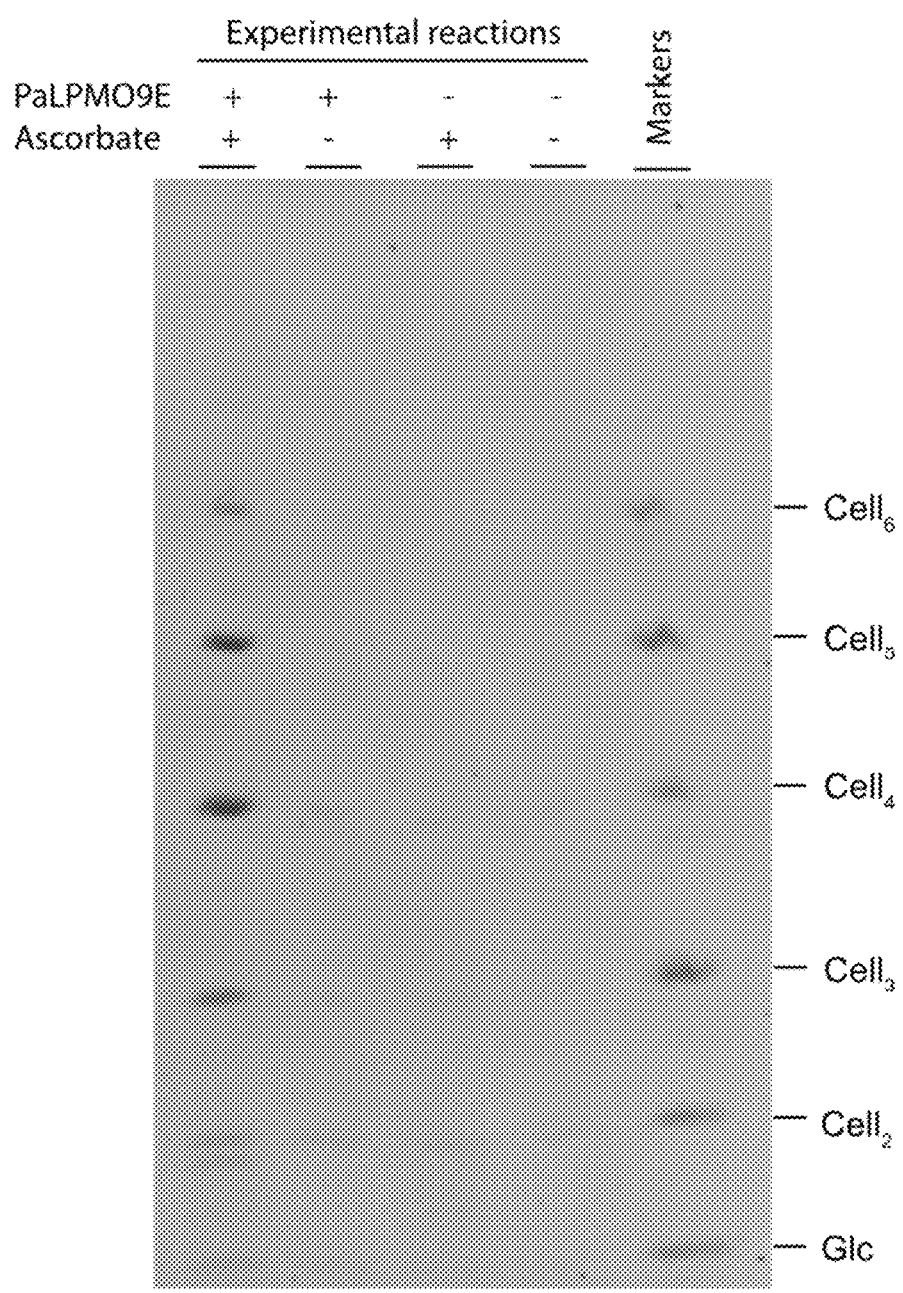
FIG. 1: PACE gel showing products of incubation of phosphoric acid-swollen cellulose with a buffered solution of PaLPMO9E and/or ascorbate, as per example 1.

The inventor has discovered enzymatic methods of producing oligosaccharides of lengths useful in foodstuff, cosmetic, or nutraceutical products without also producing substantial amounts of monosaccharides and disaccharides. Some embodiments additionally offer products with novel properties.

As used herein, "food" and "foodstuff" refer to any item destined for consumption, which may be consumption by a human, or by any other animal. It may be food, feed, a beverage, or an ingredient to be used in the production of any of the above.

As used herein, "nutraceutical" refers to any composition introduced into a human or other animal, whether by ingestion, injection, absorption, or any other method, for the purpose of providing nutrition to the human or other animal. Use in such a nutraceutical may take the form of a drink with added dietary fibre, a prebiotic additive, a pill or other capsule, tablet binding agent; or any other suitable use.

As used herein, "cosmetic" refers to any composition which is intended for use on humans or other animals to increase their aesthetic appeal or prevent future loss of aesthetic appeal, as well as any other compositions known in general parlance as cosmetics. Aesthetic appeal is not limited to visual aesthetics but applies as well to textural or any other appeal. The cosmetic may be mascara, foundation, lip gloss, eyeshadow, eyeliner, primer, lipstick blush, nail polish, bronzer, or any other makeup; shampoo, conditioner, styling mousse, styling gel, hairspray, hair dye, hair wax, or any other hair product; moisturiser, exfoliant, suncream, cleanser, toothpaste, or a cream, a lotion, ointment or any other composition effective in modifying teeth, skin, hair or other parts of the body in some aesthetic way. Or it may be a composition used as a component of a face mask, brush, hair roller, other styling device, or other solid structure, or any other suitable composition.

One step of the method of the current invention is an enzymatic reaction, in which one or more enzymes are placed in a suitable reaction vessel together with one or more feedstocks, which may be soluble or insoluble in water, and a suitable solvent.

A variety of enzymes are suitable for use in the enzymatic reaction of the current invention. Any enzyme which, when acting on a polysaccharide-containing feedstock, produces oligosaccharides while producing substantially no monosaccharides or disaccharides may be appropriate. Preferably, the enzymatic reaction comprises a lytic polysaccharide monooxygenase (LPMO), a lichenase, a xyloglucan endoglucanase (XEG), a mannanase, and/or a xylanase, such as a GH5, GH8, GH10, GH11 and/or GH30 xylanase. More preferably, the enzymatic reaction comprises an LPMO. Even more preferably, the enzymatic reaction comprises a mannanase. Yet more preferably, the enzymatic reaction comprises a xylanase, such as GH5, GH8, GH10, GH11 or GH30 xylanase. Enzyme cocktails comprising numerous enzymes are also envisaged, for example those comprising an LPMO and a xylanase, or those comprising an LPMO, a xylanase, and a lichenase or those comprising a xylanase and a mannanase. Each enzyme may be provided to the enzymatic reaction as a purified enzyme, a semi-purified mixture derived from some natural source or lab-grown culture, in the form of a microbial strain engineered to produce the enzyme, or in any other way. Fusions of these enzymes either with other enzymes or with non-enzymatic modules such as carbohydrate-binding modules (CBMs) are also envisaged within each respective term, for example an LPMO fused to a CBM, a xylanase fused to a CBM, or a xylanase fused to an LPMO.

As used herein, "lytic polysaccharide monooxygenase" and "LPMO" refer to a class of enzymes able to oxidatively cleave polysaccharides using a copper-comprising moiety and using an oxygen source, such as a molecule of dioxygen, peroxide, or any other oxygen source; and a suitable reducing agent. As such, when an LPMO is used, the enzymatic reaction may be carried out under aerobic conditions. Suitable reducing agents are not particularly limited, but examples include ascorbic acid, gallic acid, cysteine, NADH, NADPH, pyrogallol, dithiothreitol, cyanoborohydrides, borohydrides, photosynthetic pigments, lignin, lignols, and a combination of cellobiose and cellobiose dehydrogenase. While the skilled person knows a wide variety of photosynthetic pigments which may be used, thylakoids and purified fractions, or chlorophyllin, are preferred, and light may be supplied.

The reducing agent is added to the enzymatic reaction at a certain molar concentration ratio to the enzyme or enzyme cocktail. This ratio may be any suitable ratio, for example from about $10^1:1$ to about $10^8:1$, preferably from about $10^3:1$ to about $10^6:1$, more preferably from about $10^4:1$ to about $10^5:1$.

Aerobic conditions may comprise the addition of oxygen, which may be provided by aeration of the substrate mixture with an oxygen-comprising gas, such as air. Aeration may be conducted by the introduction of oxygen-comprising air bubbles into the aqueous substrate mixtures by various systems, such as an air-injector, an aeration frit, a membrane system, or an internal-loop airlift reactor. Preferably the concentration of molecular oxygen in the enzymatic reaction is from about 4 to about 14 mg/l.

As the oxidising activity of LPMOs is particularly powerful, they can oxidatively cleave even very recalcitrant polymers such as cellulose. This makes production of useful oligosaccharides possible even from feedstocks which are seen traditionally as poor source materials for food and are therefore very cheap. Examples of such feedstocks include plant biomass such as grain, grain chaff, bean pods, seed-coats, and/or other seed materials; seaweeds; corn stover, corn cob, straw, bagasse, miscanthus, sorghum residue, switch grass, bamboo, and/or other monocotyledonous tissue; water hyacinth, leaf tissue, roots, and/or other vegetative matter; hardwood, hardwood chips, hardwood pulp, softwood, softwood chips, softwood pulp, paper, paper pulp, cardboard, and/or other wood-based feedstocks; crab shells, squid biomass, shrimp shells, and/or other marine biomass; and/or any combination of appropriate feedstocks. Feedstocks suitable for producing the oligosaccharide profile of the current invention when acted on by LPMOs may comprise, for example, cellulose, chitin, chitosan, xylan and/or mannan, but any feedstock which can be suitably acted upon is envisaged.

Preferably, LPMOs are selected from the following families: AA9, AA10, AA11, AA13, AA14 and AA15. More preferably, the LPMO is PaLPMO9E (SEQ ID NO:1), an AA9 LPMO originally isolated from the ascomycete fungus *Podospora anserina* which produces particularly low levels of monosaccharides and disaccharides.

When LPMOs act on a substrate, of the two new terminal residues generated in any given cleavage reaction, one is oxidised. When LPMOs are used, cellulose, chitin, and chitosan are preferred substrates. If cellulose, for example, is the substrate, when the β-1,4 glycosidic bond is cleaved, the residue attached to the C1 carbon is converted into a lactone and the residue attached to the C4 carbon into a 4-ketoaldose. The two moieties may then spontaneously react with water to form an aldonic acid and geminal diol respectively. The resulting oligosaccharides are thus largely equivalent to β-glucans generated in any other fashion, but differ subtly in some regards. Preferably the resulting oligosaccharides comprise β-glucans and/or polymers of glucosamine.

In the case of glucans generated by LPMOs, the products may have different caramelisation properties, flavour, colour, and other properties compared to equivalents generated via non-oxidising means. As such, while they can be used in the same applications as other glucans, they provide a subtle refinement in terms of these properties which may be preferred to other sources of glucan in some applications. Similarly, use of different LPMOs yields different proportions of the different types of oxidised ends and so use of different LPMOs can enable the tailoring of oxidation to suit different food, nutraceutical and cosmetic applications.

Another exemplary enzyme useful in the invention is a lichenase, which may be selected from the GH5, GH7, GH8, GH9, GH12, GH16, GH17, or GH26 families, preferably a GH16 enzyme, more preferably a GH16 enzyme derived from *Bacillus subtilis* (SEQ ID NO:2). Claimed herein is a lichenase which produces substantially no monosaccharides or disaccharides when acting on an appropriate polysaccharide substrate such as lichenin or other mixed-linkage glucan. The enzyme is able to act on, for example, mixed linkage glucans, which are glucans comprising a mixture of β-1,3 and β-1,4 linkages, and may cleave them at β-1,4 glycosidic bonds. In the preferable case in which the lichenase acts on a mixed linkage glucan, the β-glucans produced may fall largely within the size range of from about 3 to about 7 residues, so they are particularly useful in the food, cosmetics and nutraceutical industries.

Mixed linkage glucans are abundant in members of the grass and horsetail families, and as such, grass-based feedstocks such as straw have high levels of it, and may be acted upon usefully with lichenases.

Another alternative enzyme useful in the invention is a xylanase of the GH5, GH8, GH10, GH11 and/or GH30 family, which may act on, for example, feedstocks comprising a xylan backbone. The xylanase may be, for example, a glucuronoxylanase, an arabinoxylanase, or a glucuronoarabinoxylanase. The enzyme may be active on a variety of polymers having a xylan backbone, such as glucuronoxylan, arabinoxylan, and glucuronoarabinoxylan. These polymers are abundant in various plant-derived feedstocks, for example both hardwood and softwood may comprise appropriate polysaccharides, with hardwood often comprising glucuronoxylan and softwood often arabinoglucuronoxylan. Preferred xylanases include GH5 xylanases from *Ruminiclostridium thermocellum* (SEQ ID NO:3) and *Gonapodya prolifera* (SEQ ID NO:4), and GH30 xylanases from *Dickeya chrysanthemi* (SEQ ID NO:5), *Bacillus subtilis* (SEQ ID NO:6) and *Bacteroides ovatus* (SEQ ID NO:7).

Feedstocks comprising softwood arabinoglucuronoxylan are preferred feedstocks, and when digested with GH30 xylanases the products comprise oligosaccharides having a main chain of a length useful in the foodstuff, cosmetics, and nutraceutical industries. These oligosaccharides may comprise more than about five main chain residues and substantially no monosaccharides or disaccharides.

Feedstocks comprising hardwood glucuronoxylan are another preferred feedstock, and when digested with GH30 xylanases the products comprise glucuronoxylan chains largely comprising from about 5 to about 30 main chain residues.

Other enzymes useful in the invention include xyloglucanases and xyloglucan endoglucanases (XEGs), which are produced by numerous organisms, including plant-pathogenic microbes. They are able to act on xyloglucan, a hemicellulosic β-1,4 glucan chain abundant in the primary cell wall of higher plants, which is decorated with xylose, some of the xylose residues being further decorated with other residues, such as galactose. When appropriate xyloglucanases or XEGs act on xyloglucan, the products comprise xyloglucan oligosaccharides having a main chain of a length useful in the foodstuff, cosmetics, and nutraceutical industries, and comprise substantially no monosaccharides or disaccharides. One preferable xyloglucanase is a GH5 xyloglucanase from *Bacteroides ovatus* (SEQ ID NO:8).

The enzymatic reaction may take place in solution and/or suspension, in a suitable reaction vessel. At a temperature or temperature protocol appropriate for the particular combination of enzyme and feedstock, the reaction may be allowed to progress for a certain amount of time, or until the products have reached a desired concentration, or until some other requirement has been met.

As used herein, "suspension" refers to a composition comprising at least two immiscible phases, for example, a solid and a liquid phase, wherein the weight of the solid phase may be, as a percentage of the weight of the composition, in the range of from about 0.5% to about 30%, preferably 1% to about 10%, more preferably from about 2% to about 7%, yet more preferably from about 3% to about 5%. The suspension may comprise a suitable solvent, which is preferably water. It may be particularly beneficial to use a slightly higher concentration, for instance to improve process time, of from about 1% to about 35%, preferably 5% to about 30%, more preferably from about 8% to about 25%, yet more preferably from about 10% to about 20%.

In order to ensure optimal contact between the enzymes and feedstock, the reaction mixture may be agitated, either constantly or at intervals. The agitation may take the form of rhythmically moving the entire reaction vessel, of a fan or other stirring device, of a bubble sparging, or any other method of agitation.

The enzymatic reaction may be a microbial fermentation. The temperature and reaction time will be suitable for the growth of the microbial organism used. The microbial organism may be genetically altered to produce an enzyme suitable for the production of an oligosaccharide of the present invention, while producing substantially no monosaccharides or disaccharides. The microbe may be, for example, a bacterium, for example *Escherichia coli*, or a fungus, such as *Saccharomyces cerevisiae*.

Further embodied in the present invention is an expression vector suitable for modifying the subject microorganism such that it produces an enzyme or mixture of enzymes of the current invention. Where desired, the expression vector, which may be a plasmid or any other nucleic acid able to induce production of the enzyme, may comprise one or more of the following regulatory sequences so as to control the expression of the exogenous enzyme: regulatory sequences of a heat shock gene, regulatory sequences of a toxicity gene, and regulatory sequences of a spore formation gene.

The enzymatic reaction is carried out at a temperature or temperature protocol appropriate to the enzymes and substrates used. For example, it may be carried out at a constant temperature in the range of from about 10° C. to about 80° C., preferably about 20° C. to about 60° C., more preferably from about 30° C. to about 40° C. It may be particularly beneficial to use a slightly higher temperature, for instance to improve process time, of about 30° C. to about 70° C., preferably from about 40° C. to about 60° C. If the enzymatic reaction takes the form of a microbial fermentation the temperature may be appropriate for such, for example the enzymatic reaction may comprise the growth of E. coli and/or the temperature may be constant and approximately 37° C.

The pH of the solution or suspension may affect the activity of the enzymes. Control of pH may be important in assuring that an enzymatic reaction proceeds at a suitable rate. The enzymatic reaction of the present invention may take place at a pH in the range of from about 2 to about 10, preferably about 3 to about 8, more preferably about 4 to about 6.

The enzymatic reaction is allowed to continue for a certain time period before optionally being quenched, and the products isolated or otherwise collected. This time period may be from about 1 minute to about 5 days, and is preferably from about 0.5 days to about 3 days, more preferably from about 16 hours to about 48 hours. The reaction may alternatively be allowed to proceed until completion or approximate completion of the reaction. If the reaction is allowed to continue until completion or approximate completion of the reaction, this may be longer than 5 days.

The one or more feedstocks added to the enzymatic reaction comprise polysaccharides. Such polysaccharides may have been produced by a separate reaction proceeding simultaneously in the reaction vessel. The polysaccharides present in the enzymatic reaction are cleaved by enzymes into useful oligosaccharides.

Any substance which comprises appropriate polysaccharides may form part of the feedstock. As the foodstuff, cosmetic, and nutraceutical industries use a broad variety of oligosaccharides, the polysaccharides appropriate for taking part in the enzymatic reaction are not particularly limited. Preferably, the feedstock comprises one or more polysaccharide selected from cellulose, chitin, chitosan, mixed-linkage glucan, xylan, and xyloglucan. If xylans are present, they preferably comprise glucuronoxylan, arabinoxylan, and/or glucuronoarabinoxylan.

The feedstocks comprising such polysaccharides are also not particularly limited, as most plant matter is rich in such polymers. As such, the feedstock may comprise plant biomass such as grain, grain chaff, bean pods, seed-coats, and/or other seed materials; seaweeds; corn stover, corn cob, straw, bagasse, miscanthus, sorghum residue, switch grass, bamboo, and/or other monocotyledonous tissue; water hyacinth, leaf tissue, roots, and/or other vegetative matter; hardwood, hardwood chips, hardwood pulp, softwood, softwood chips, softwood pulp, paper, paper pulp, cardboard, and/or other wood-based feedstocks; crab shells, squid biomass, shrimp shells, and/or other marine biomass, and/or any combination of appropriate feedstocks. Preferably, the feedstock comprises wheat straw or wood. As any given natural feedstock is likely to comprise a mixture of different polysaccharides, it will sometimes be the case that a cocktail of different enzymes is beneficial. Such a cocktail may comprise any other enzyme. For example, such a cocktail might comprise a cellulase with a xylanase, a cellulase with a mannanase, a xylanase with a mannanase, an LPMO with a xylanase, an LPMO with a lichenase, an LPMO with a mannanase, or an LPMO with a different LPMO in which the enzyme partners are present in molar ratios preferably between 1:10 and 10:1. In addition, as many appropriate feedstocks are recalcitrant, pre-treatment of the feedstock is envisaged.

As used herein, "pre-treatment" is any process which makes a feedstock more easily acted upon by the enzymes inherent in the enzymatic reaction step of the current invention. The pre-treatment occurs before the enzymatic reaction, and may comprise acid treatment by, for example, sulphuric acid, phosphoric acid, or trifluoroacetic acid; alkali treatment by, for example, sodium hydroxide, or ammonia fibre expansion; heat treatment by, for example, hot water, hot steam, or hot acid; and/or enzyme treatment by, for example, a hydrolase, lyase, or LPMO, or any mixture of the above processes.

As used herein, "polysaccharide" refers to a saccharide polymer of any length greater than two residues. Polysaccharides may be highly branched, lightly branched, or unbranched, may comprise any manner of glycosidic bond in any combination, any number of, for example, a or 6 linkages, and any combination of monomer types, such as glucose, glucosamine, mannose, xylose, galactose, fucose, fructose, glucuronic acid, arabinose, or derivatives thereof such as any combination of the above monomers decorated with acetyl or other groups. The polysaccharide may be a cellulosic or hemicellulosic polymer, hemicellulosic polymers envisaged including xylan, glucuronoxylan, arabinoxylan, glucomannan, and xyloglucan. Cellulose is the preferred cellulosic polymer. Mannan is preferred even more so. Xylan is preferred yet more still.

As used herein "highly branched", "lightly branched", and "unbranched" refer to the number of side-chains per stretch of main chain in a saccharide. Highly branched saccharides have on average from 4 to 10 side chains per 10 main-chain residues, slightly branched saccharides have on average from 1 to 3 side chains per 10 main-chain residues, and unbranched saccharides have only one main chain and no side chains. The average is calculated by dividing the number of side chains in a saccharide by the number of main-chain residues.

As used herein, "saccharide" refers to any polysaccharide, oligosaccharide, monosaccharide, or disaccharide.

As used herein, "oligosaccharide" refers to saccharide polymers having chain lengths generally within the range which is useful in the context of a foodstuff, cosmetic, or nutraceutical product. They are comprised at least within the products of the enzymatic reaction. Typical chain lengths may be from about 3 to about 16 saccharide residues. Oligosaccharides may be highly branched, lightly branched, or unbranched, may comprise glycosidic bonds in any combination, any number of a or 13 linkages, and any combination of monomer types, such as glucose, glucosamine, mannose, xylose, galactose, fucose, fructose, glucuronic acid, arabinose, or derivatives thereof. Suitable derivatives include the above monomers comprising acetyl or other groups.

The oligosaccharides produced in the process of the present invention fall within an upper and a lower size limit. The lower size limit is that substantially no monosaccharides or disaccharides are produced.

As used herein, "substantially no" monosaccharides or disaccharides refers to a set of products in which by weight less than about 60%, preferably less than about 50%, preferably less than about 40%, more preferably less than about 30%, even more preferably less than about 20%, even more preferably less than about 15%, even more preferably less than about 10%, even more preferably less than about 5%, even more preferably less than about 2%, yet more preferably less than about 1%, most preferably less than about 0.1%, of the imageable saccharides are monosaccharides or disaccharides.

As described herein, the enzymatic reaction of the invention is useful to produce oligosaccharides whilst producing substantially no monosaccharides and disaccharides. However, it is envisaged that the reaction will take place in a large vessel with other reactions (e.g. enzymatic) taking place at the same time. These other enzymatic reactions will also be breaking down polysaccharides into smaller saccharides, including oligosaccharides, but may also produce monosaccharides and disaccharides. Thus, the method further comprises a second enzymatic reaction comprising contacting a second polysaccharide-cleaving enzyme to the one or more polysaccharide-containing feedstocks, which may produce one or more disaccharides. In some instances monosaccharides may also be produced. These monosaccharides and disaccharides may be included in the ingredient, thus in a specific feature, suitably the amount of disaccharides in the produced ingredient is less than about 50%, preferably less than about 40%, more preferably less than about 35%, more preferably less than about 30%, even more preferably less than about 25%, even more preferably less than about 20%, even more preferably less than about 15%, even more preferably less than about 10%, yet even more preferably less than about 5% of the imageable saccharides.

Suitably the amount of monosaccharides in the produced ingredient is less than about 25%, preferably less than about 20%, more preferably less than about 15%, even more preferably less than about 10%, even more preferably less than about 5%, yet even more preferably less than about 3%, yet even more preferably less than about 1% of the imageable saccharides.

As used herein, "imageable polysaccharides" are those which are visible in the gel or spectrum when one of the following imaging protocols is carried out.

One way of assessing the percentages by weight of different polysaccharides produced by the current invention is processing a sample of the enzymatic reaction products to derivatise their reducing ends with a fluorophore followed by polyacrylamide gel electrophoresis, before imaging the resulting polyacrylamide gel, for example by fluorescence imaging, and conducting optical density analysis on each band, the resulting value to be adjusted by residue-count to give an indication of mass. The skilled person will be able to carry this out with the information inside this application, in conjunction with Goubet et al. (2002). This is the method envisaged for calculating percentage values by weight of imageable polysaccharides.

Another way of assessing the percentages by weight of different polysaccharides produced by the current invention is to analyse by high-throughput liquid chromatography, for example using an anion exchange chromatography column in an alkaline solution, followed by pulsed amperometric detection. The resulting data can be adjusted by residue-count to give an indication of mass. The skilled person will be able to carry this out with the information inside this application, in conjunction with Simmons et al. (2013).

As used herein "monosaccharide" and "disaccharide" refer to saccharide compounds consisting respectively of one or two residues. Monosaccharides are compounds such as glucose, glucosamine, xylose, galactose, fucose, fructose, glucuronic acid, arabinose, galacturonic acid; or epimers or other derivatives thereof. Suitable derivatives include acetyl or other groups. Disaccharides are compounds consisting of two monosaccharides joined via any glycosidic bond. Envisaged herein are enzymes or combinations of enzymes producing substantially no monosaccharides or disaccharides in such a reaction.

The upper size limit of the oligosaccharides depends on the enzymes, feedstock, and reaction conditions used, and may be that the weight of products comprising 16 or more residues in their main chain is below a certain percentage of the weight of imageable polysaccharides.

This percentage may be about 15%, preferably less than about 10%, more preferably less than about 5%, even more preferably less than about 2%, most preferably less than about 1%; or, it may be that the weight of products comprising 15 or more residues in their main chain is below about 15%, preferably less than about 10%, more preferably less than about 5%, even more preferably less than about 2%, most preferably less than about 1%, of the weight of imageable polysaccharides; or it may be that the weight of products comprising 14 or more residues in their main chain is below about 15%, preferably less than about 10%, more preferably less than about 5%, even more preferably less than about 2%, most preferably less than about 1%, of the weight of imageable polysaccharides, or, in increasing order of preference, that this is the case with products comprising 13, 12, 11, 10, 9, 8, or 7 residues.

The feedstock may comprise cellulose, and when acted on by LPMOs or other enzymes, the weight of products comprising 7 or more residues in their main chain may be below about 15%, preferably less than about 10%, more preferably less than about 5%, even more preferably less than about 2%, most preferably less than about 1%, of the weight of imageable polysaccharides. Or it may be that the weight of products comprising 8 or more residues in their main chain may be below about 15%, preferably less than about 10%, more preferably less than about 5%, even more preferably less than about 2%, most preferably less than about 1%, of the weight of imageable polysaccharides.

The feedstock may comprise chitin, and when acted on by LPMOs or other enzymes, the weight of products comprising 11 or more residues in their main chain may be below about 15%, preferably less than about 10%, more preferably less than about 5%, even more preferably less than about 2%, most preferably less than about 1%, of the weight of imageable polysaccharides. Or it may be that the weight of products comprising 12 or more residues in their main chain may be below about 15%, preferably less than about 10%, more preferably less than about 5%, even more preferably less than about 2%, most preferably less than about 1%, of the weight of imageable polysaccharides.

The feedstock may comprise chitin, and when acted on by LPMOs or other enzymes, the weight of products having only 3 or fewer residues in their main chain may be below about 15%, preferably less than about 10%, more preferably less than about 5%, even more preferably less than about 2%, most preferably less than about 1%, of the weight of imageable polysaccharides.

The feedstock may comprise mixed-linkage glucan, and when acted on by lichenase or other enzymes, the weight of products comprising 6 or more residues in their main chain may be below about 15%, preferably less than about 10%, more preferably less than about 5%, even more preferably less than about 2%, most preferably less than about 1%, of the weight of imageable polysaccharides. Or it may be that the weight of products comprising 7 or more residues in their main chain may be below about 15%, preferably less than about 10%, more preferably less than about 5%, even more preferably less than about 2%, most preferably less than about 1%, of the weight of imageable polysaccharides.

The feedstock may comprise xylan, preferably glucuronoxylan, arabinoxylan, or arabinoglucuronoxylan, more preferably hardwood glucuronoxylan or softwood arabinoglucuronoxylan.

The xylan may comprise arabinoglucuronoxylan, preferably softwood arabinoglucuronoxylan, and when acted on by a xylanase, such as a GH30 xylanase, or other enzyme, the weight of products comprising 9 or more residues in their main chain may be below about 15%, preferably less than about 10%, more preferably less than about 5%, even more preferably less than about 2%, most preferably less than about 1%, of the weight of imageable polysaccharides. Or it may be that the weight of products comprising 10 or more residues in their main chain may be below about 15%, preferably less than about 10%, more preferably less than about 5%, even more preferably less than about 2%, most preferably less than about 1%, of the weight of imageable polysaccharides.

The xylan may comprise arabinoglucuronoxylan, preferably softwood arabinoglucuronoxylan, and when acted on by a xylanase, such as a GH30 xylanase, or other enzyme, the weight of products having only 5 or fewer residues in their main chain may be below about 15%, preferably less than about 10%, more preferably less than about 5%, even more preferably less than about 2%, most preferably less than about 1%, of the weight of imageable polysaccharides.

The feedstock may comprise glucuronoxylan, preferably hardwood glucuronoxylan, and when acted on by xylanase, such as a GH30 xylanase, or another enzyme, the weight of products comprising 31 or more residues in their main chain may be below about 15%, preferably less than about 10%, more preferably less than about 5%, even more preferably less than about 2%, most preferably less than about 1%, of the weight of imageable polysaccharides.

The feedstock may comprise hardwood glucuronoxylan, preferably hardwood glucuronoxylan, and when acted on by xylanase, such as a GH30 xylanase, or another enzyme, the weight of products having only 4 or fewer residues in their main chain may be below about 15%, preferably less than about 10%, more preferably less than about 5%, even more preferably less than about 2%, most preferably less than about 1%, of the weight of imageable polysaccharides.

The feedstock may comprise xyloglucan, and when acted on by XEG or other enzymes, the weight of products comprising 6 or more residues in their main chain may be below about 15%, preferably less than about 10%, more preferably less than about 5%, even more preferably less than about 2%, most preferably less than about 1%, of the weight of imageable polysaccharides. Or it may be that the weight of products comprising 7 or more residues in their main chain may be below about 15%, preferably less than about 10%, more preferably less than about 5%, even more preferably less than about 2%, most preferably less than about 1%, of the weight of imageable polysaccharides Where branched polymers are being described in terms of residue count, the number of residues refers only to the longest chain of residues, and does not include any side chains.

After the enzymatic reaction has progressed to a desired point, the products may be handled in a variety of ways. As the reaction mixture will often comprise a mixture of soluble and insoluble products, with at least some of the original feedstock often also remaining, the reaction mixture may be filtered to remove insoluble matter and prepare the soluble products for further processing.

When used herein and otherwise unqualified, "soluble", "solubility" and grammatical variants refer to solubility in water.

The desired oligosaccharides may also be isolated from the enzymatic reaction mixture in a number of ways. They may be isolated based on solubility, so that a composition of soluble saccharides only is extracted for further processing, and/or isolated chromatographically to produce a composition with a narrower band of oligosaccharide chain lengths. Isolation may for example be based on precipitation, size-exclusion chromatography, ion-exchange chromatography, or filtration, including ultrafiltration and nanofiltration. In the case that isolation based on solubility is carried out, the profile of saccharides present in the isolated composition will depend on the original enzymatic reaction, as different polysaccharides decrease in solubility with length at different rates.

Also envisaged in the scope of the invention is the further treatment of the produced oligosaccharides to produce further products before incorporation into a foodstuff, cosmetic, or nutraceutical. This further treatment may comprise any chemical, physical, or enzymatic step, such as reduction, preferably reductive amination where appropriate; oxidation, caramelisation, modification with a Schiff base, or via the Maillard reaction, or by any combination of such steps, and may provide different products having properties which are improved for the desired purpose. For example the caramelisation properties, calorific value, flavour, and colour may be modified.

The products of the one or more enzymatic reactions may be deemed an ingredient suitable for incorporation into a foodstuff, cosmetic, or nutraceutical at any stage of this process. For example, the reaction mixture itself, after the desired time limit or other condition for completion has been met, may directly be deemed the ingredient, or either the solid or liquid component of the filtered products may be the ingredient, or the composition of isolated oligosaccharides may be the ingredient, or the oligosaccharides having undergone further treatment may be the ingredient.

As used herein, "ingredient" is any composition suitable for incorporation into a foodstuff, cosmetic, or nutraceutical product, which may include those which are used directly as the product itself.

The present ingredient suitable for incorporation into a foodstuff, cosmetic, or nutraceutical may be usable directly as a foodstuff, cosmetic, or nutraceutical product, or it may be mixed with other ingredients to form a foodstuff, cosmetic, or nutraceutical. The ingredient may also be treated in some physical or chemical way before or during incorporation into a foodstuff, cosmetic, or nutraceutical. It may be directly incorporated into a product, or it may be incorporated into, for example, a dough, cake mixture, chocolate mixture or other food precursor; a cosmetic base composition; or a nutraceutical, and be optionally cooked or otherwise treated in a way which may cause chemical modification, a change of texture, a change of colour, or other modification.

Once a composition of the oligosaccharide products suitable for the application being considered is obtained, and further treatment and/or isolation is optionally carried out, the derivation of a foodstuff, cosmetic, or nutraceutical from the composition furnishes a very broad array of potential uses. The ingredients of the current invention are useful in applications in which oligosaccharides are conventionally used. They are particularly useful in applications in which monosaccharides and disaccharides are detrimental and would otherwise be considered for removal.

The invention includes a foodstuff, cosmetic, or nutraceutical comprising or produced from the ingredient of the current invention.

For example, in the food industry oligosaccharides produced by the current method may be used as sweeteners, bulking agents, added dietary fibre, or humectants. They may be incorporated into cakes, bread, or other baked goods, or into chocolate or other confectionery such as toffee, fudge, meringue, or caramel; or drinks, for example to provide favourable taste or colour characteristics or to increase dietary fibre content. Or they may be incorporated into animal feed, for example either as an isolated ingredient or by utilising the enzymatic reaction mixture directly as feed.

Of particular note is the use as a sweetening agent. As monosaccharides and disaccharides contribute to dental disease, calorific excess, obesity, and diabetes, and potentially behavioural issues, in certain applications food manufacturers would prefer not to include monosaccharides and disaccharides in their products. The oligosaccharides of the current invention, as their production method produces substantially no monosaccharides or disaccharides, may be used as sweetening agents, allowing foodstuffs to be sweet without exerting the detrimental effects of monosaccharides and disaccharides.

In the cosmetics industry, monosaccharides and disaccharides may contribute to spoilage if not removed at some stage of manufacture, while oligosaccharides are useful as ingredients, as they may improve texture and moisture retention, act as UV-absorbing molecules, maintain a gel or cream structure, and/or serve as bulking agents. Thus, the present invention includes a foodstuff, cosmetic, or nutraceutical comprising the oligosaccharide-containing ingredient obtainable by the method of the invention.

The oligosaccharides of the present invention are useful when incorporated into nutraceutical compositions, as the dietary fibre they provide without substantial concomitant provision of dietary sugar has been shown to encourage digestive health, well-regulated gut flora, and other benefits to wellbeing. In this context they may also function as an ingredient in a probiotic drink or other prebiotic or probiotic formulation.

EXAMPLES

Example 1—Manufacturing Oligosaccharides from Cellulose Using an LPMO

1. Phosphoric acid-swollen cellulose (PASO) was prepared by making a slurry of 1 g Avicel cellulose (Sigma-Aldrich) with 3 ml $H_2O$ before adding 30 ml ice-cold phosphoric acid and incubating at 0° C. for 1 h. The cellulose was then washed numerous times with water until the flowthrough had a neutral pH before use in reactions.

2. Apo-PaLPMO9E (SEQ ID NO:1) was pre-incubated for 0.5-1 h at 5° C. in 0.9 stoichiometric $Cu(II)(NO_3)_2$ immediately before enzyme reactions.

3. 25 μg PASO, 30 μg PaLPMO9E (pre-loaded with copper) and 500 nmol ascorbate were incubated in 100 μl 100 mM ammonium acetate pH 6 for 32 hours at 50° C. with intermittent shaking.

4. Samples were centrifuged and supernatants were dried in vacuo.

5. Supernatants were reductively labelled with ANTS and analysed by PACE (as per Goubet et al. 2002). FIG. 1 shows the resulting gel.

Example 2—Manufacturing Oligosaccharides from Mixed-Linkage Glucan Using a Lichenase and Incorporation of Said Oligosaccharides into a Cake 1. 250 g ground porridge oat powder was boiled in 2 l water for 30 min.

2. Once cooled, 2 l ice-cold 96% (v/v) ethanol was added and the suspension was allowed to sit overnight at 5° C. The suspension was filter through miracloth until dry, resuspended in 50% (v/v) ethanol and again filtered through miracloth.

3. The remaining mass was boiled in 1 l water and incubated for 16 h at 30° C. with 2000 U of lichenase from *Bacillus subtilis* (SEQ ID NO:2, Megazyme).

4. Once cooled, 2 l ice-cold 96% (v/v) ethanol was added and the suspension was allowed to sit overnight.

Figure 2:
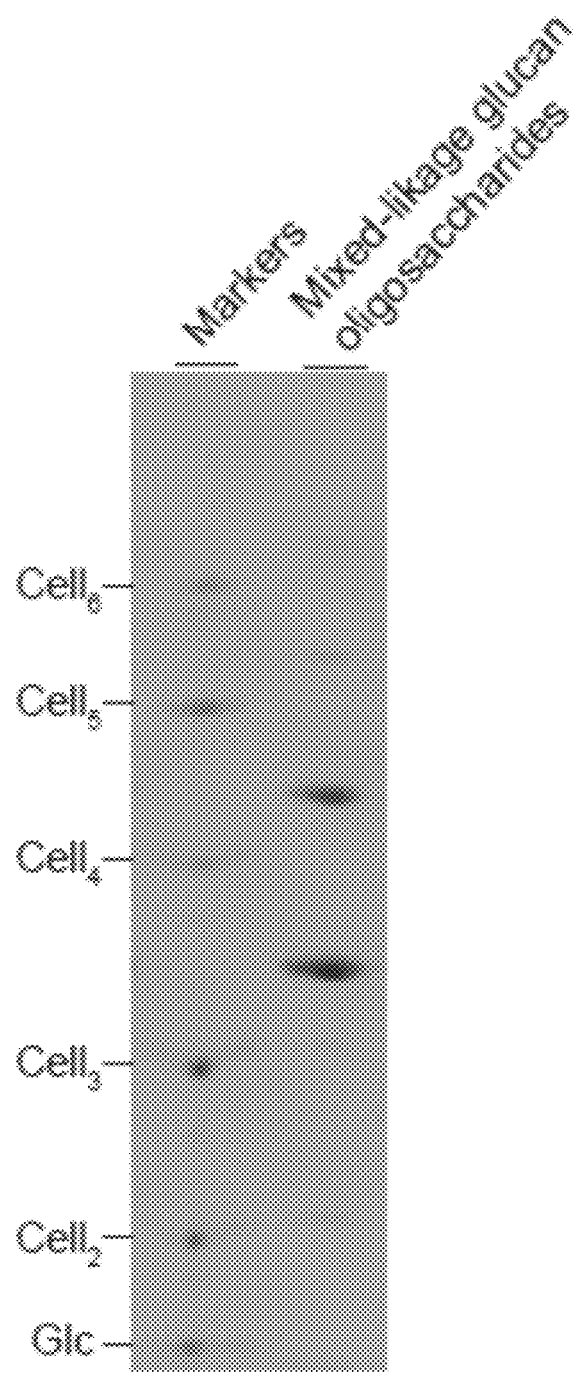
FIG. 2: PACE gel showing products of incubation of washed oats with a solution of GH16 lichenase from *Bacillus subtilis*, as per example 2.

5. The supernatant was collected by centrifugation and dried in vacuo, yielding 5.2 g mixed-linkage glucan oligosaccharides. An aliquot was reductively labelled with ANTS and analysed by PACE. FIG. 2 shows the resulting gel.

6. One medium egg was beaten with 50 g butter and 50 g plain flour.

7. 3 g of the mixture was taken and mixed with 1 g of sugar.

8. 3 g of the mixture was taken and mixed with 1 g of mixed-linkage glucan oligosaccharides.

9. 4 g of the mixture was taken and not mixed further with anything.

10. All three batter mixtures were baked on a baking tray in a pre-heated oven at 180° C. for 5 min.

Figure 3:
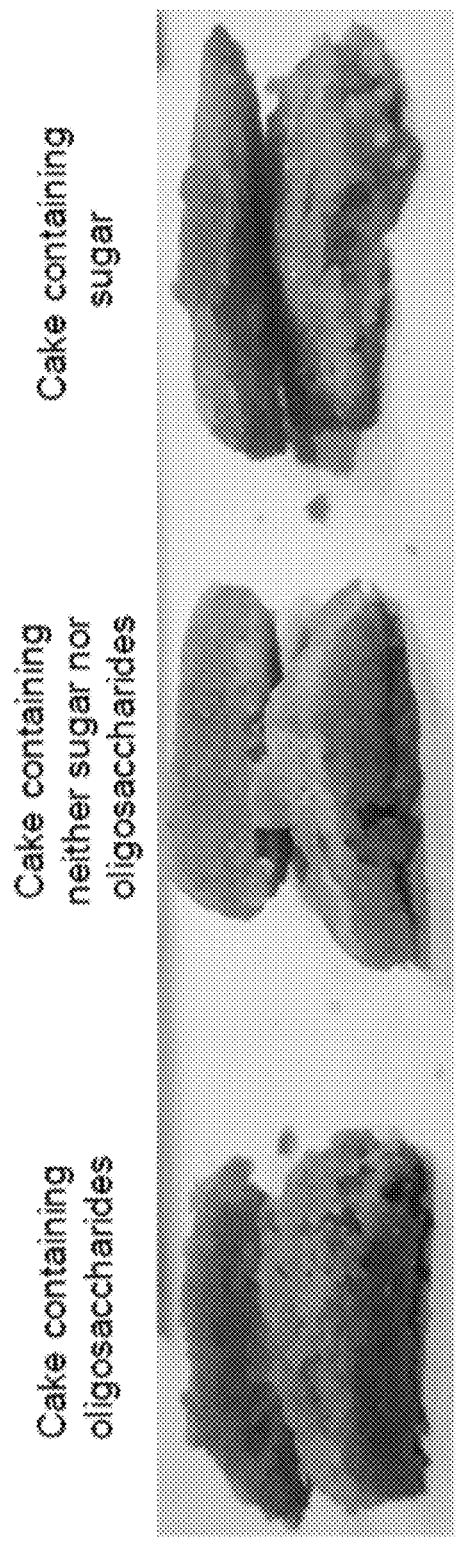
FIG. 3: Photo of cakes made by incorporating into the cake batter sugar, mixed-linkage glucan oligosaccharides or neither sugar nor oligosaccharide, as per example 2.

11. After baking, the cakes were cooled, photographed and tasted. FIG. 3 shows the photograph.

12. The cake without added sugar or oligosaccharide was unable to hold the butter inside, which instead leaked out during baking. It has a smooth surface and doughy texture similar to pie pastry, and had a savoury flavour.

The cake containing sugar held butter well and had a more crumbly and spongy texture and surface, characteristic of cakes. It also became brown and crisp at the edges. It had a very sweet taste.

Similar to the sugar-containing cake, the cake containing mixed linkage glucan oligosaccharides held butter well and had a characteristically cake-like texture and surface. It also became brown and crisp at the edges like the sugar-containing cake. It was sweeter than the cake without added sugar or oligosaccharides, but not as sweet as the cake containing sugar.

Example 3—Manufacturing Oligosaccharides from Xylan Using a GH30 Xylanase

1. Spruce wood chips were blended in suspension in a food blender until they broke into small particles, and then ball-milled.

2. 100 µl reaction mixtures containing 3.3 mg ball-milled spruce wood chips and 100 mM ammonium acetate pH6 were incubated for 16 h at 30° C. with (or without) 5 µg *Ruminiclostridium thermocellum* GH30 (sourced from NZYTech).

Figure 4:
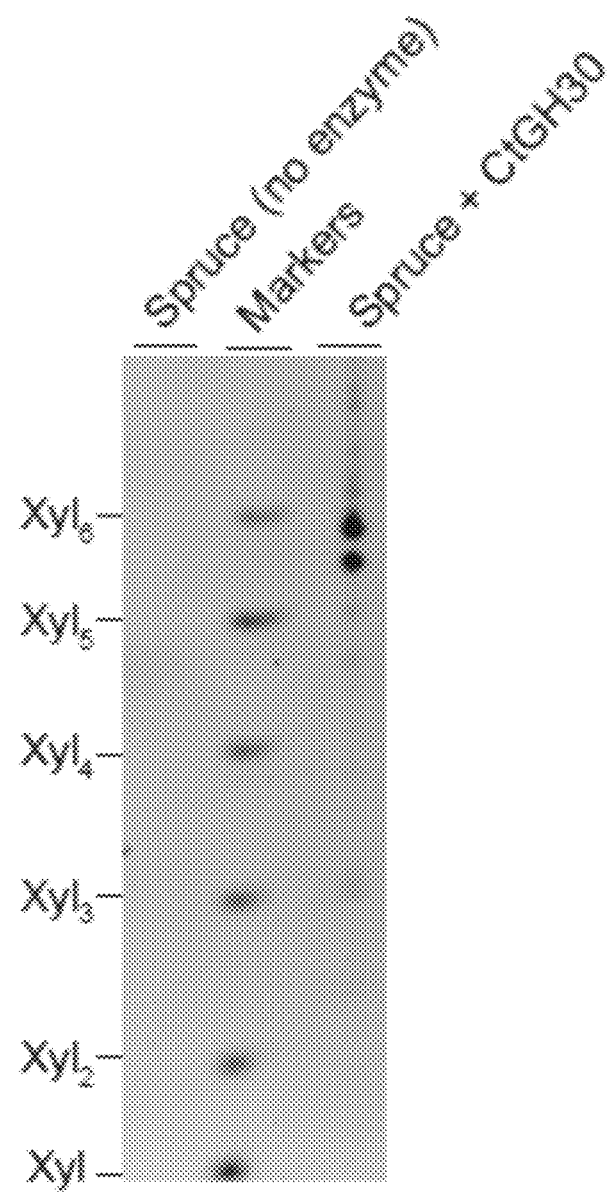
FIG. 4: PACE gel showing products of incubation of spruce wood chips with a buffered solution of GH30 xylanase from *Ruminiclostridium thermocellum*, as per example 3.

3. Reaction products were reductively labelled with ANTS and analysed by PACE. FIG. 4 shows the resulting gel.

Example 4—Manufacturing Oligosaccharides from Xyloglucan Using a Xyloglucanase 1. 100 µl reaction mixtures containing 1% (w/v) tamarind xyloglucan and 100 mM ammonium acetate pH6 were incubated for 16 h at 30° C. with (or without) 0.1 U xyloglucanase (GH5, CAS: 76901-10-5) from *Paenibacillus* sp. (Megazyme).

Figure 5:
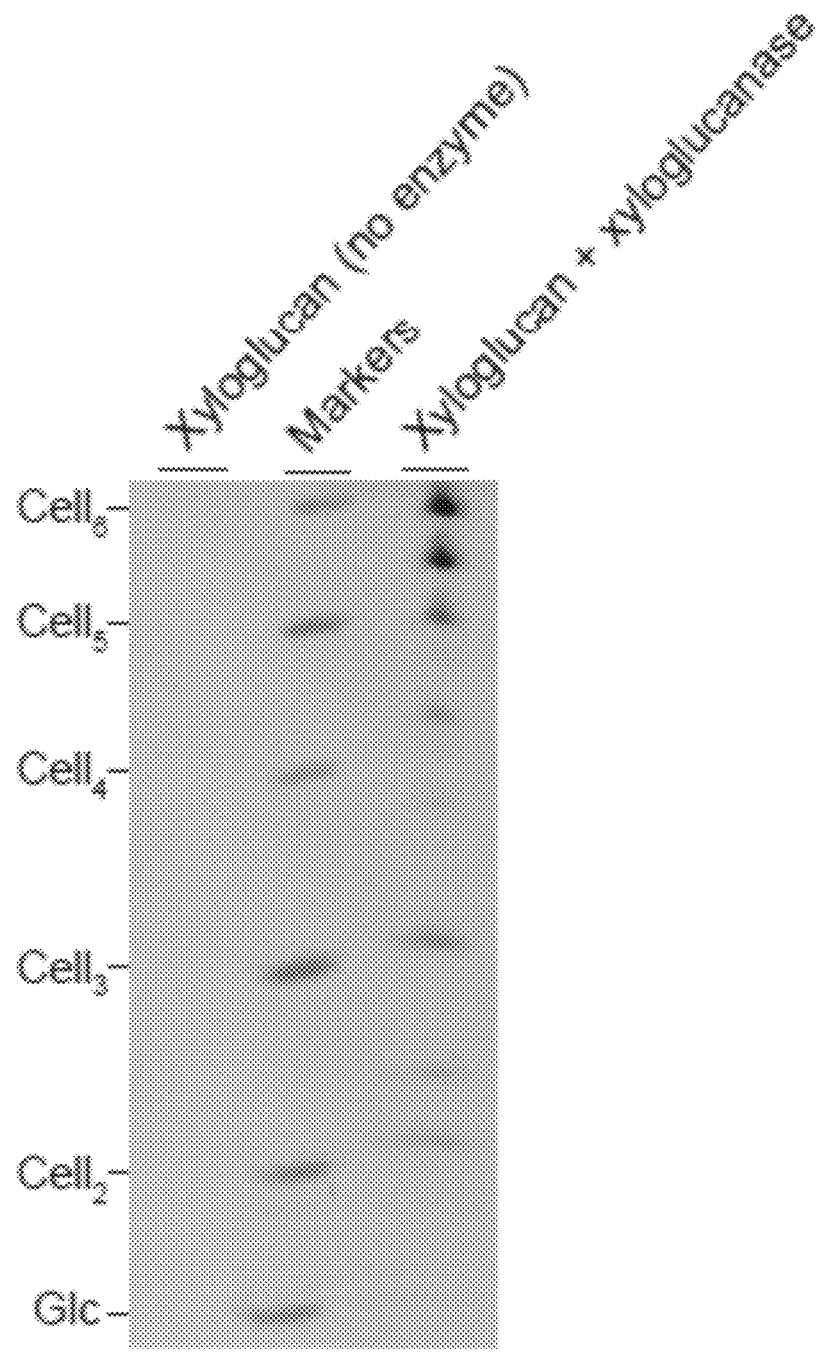
FIG. 5: PACE gel showing products of incubation of tamarind xyloglucan with a buffered solution of GH5 xyloglucanase from *Paenibacillus* sp, as per example 4.

2. Reaction products were reductively labelled with ANTS and analysed by PACE. FIG. 5 shows the resulting gel.

Prophetic Example 5: Banana Bread Baked Using the Disclosed Foodstuff Ingredient A basic banana bread recipe making 10 servings, consists of one cup (US) (192 g) of sugar (i.e. granulated pure cane sugar for drinks and cereal, such as that provided by Tate and Lyle), 113.5 g of butter, three ripe bananas, three eggs, two cups of all-purpose flour, 1 tea spoon of baking soda and ½ tea spoon of salt.

An oven is preheated to 190° C. The bananas are mashed in a bowl using a fork. In a separate bowl, the flour, baking soda and salt are mixed. The butter and sugar are whisked until combined and creamed. The mashed bananas are added and mixed well followed gradually by the whisked eggs until well blended. Then, the flour mixture is folded in. The mixture is poured into a greased baking loaf tin and baked for 45 mins, or until an inserted toothpick comes out clean. The basic bread is cooled on a cooling rack. The bread is cut into 10 portions.

Banana bread A is prepared using the same recipe as the basic banana bread, except 30% of the sugar is replaced with the disclosed ingredient of the invention, so 134 g of cane sugar and 58 g of the disclosed ingredient of the invention are used.

Banana bread B is prepared using the same recipe as the basic banana bread, except 50% of the sugar is replaced with the disclosed ingredient of the invention, so 96 g of cane sugar and 96 g of the disclosed ingredient of the invention are used.

Banana bread C is prepared using the same recipe as the basic banana bread, except 100% of the sugar is replaced with the disclosed ingredient of the invention, so 0 g of cane sugar and 192 g of the disclosed ingredient of the invention are used.

Results

The nutritional values of the banana breads are shown in Table 1. These are calculated using USDA National Nutrient Database for Standard Reference Legacy Release, April 2018 (https://ndb.nal.usda.gov/ndb/search/list?home=true) using the following records: eggs (NDB Id 01123), cane sugar (NDB Id 45167812), butter (NDB Id 01145), bananas (NDB Id 09040), all-purpose flour (NDB Id 45054364), baking soda (NDB Id 18372), table salt (NDB Id 02047) and considering the whole recipe making 10 servings.

There is an 8% calorie reduction for bread A compared to the basic bread, a 30% reduction of added sugar and a 24% reduction in total sugar. There is a 12% calorie reduction for bread B compared to the basic bread, a 50% reduction of added sugar and a 39% reduction in total sugar. There is a 25% calorie reduction for bread C compared to the basic bread, a 100% reduction of added sugar and a 79% reduction in total sugar.

TABLE 1

Nutritional value of one portion of each of the banana breads described.

| | Basic bread (one portion) | Bread A (one portion) | Bread B (one portion) | Bread C (one portion) |
|---|---|---|---|---|
| Protein (g) | 4.5 | 4.5 | 4.5 | 4.5 |
| Fat (g) | 10.5 | 10.5 | 10.5 | 10.5 |
| Carbohydrate (g) | 45.8 | 45.8 | 45.8 | 45.8 |
| Fiber (g) | 1.7 | 1.7 | 1.7 | 1.7 |
| Sugar (g) | 24.4 | 18.6 | 14.8 | 5.2 |
| Calories (kcal) | 291.5 | 269.9 | 255.5 | 219.5 |

REFERENCES

Goubet F, Jackson P, Deery M J, Dupree P. Polysaccharide analysis using carbohydrate gel electrophoresis: a method to study plant cell wall polysaccharides and polysaccharide hydrolases. *Anal Biochem.* 2002, 53-68

Simmons T J, Uhrín D, Gregson T, Murray L, Sadler I H, Fry S C. An unexpectedly lichenase-stable hexasaccharide from cereal, horsetail and lichen mixed-linkage β-glucans (MLGs): Implications for MLG subunit distribution Phytochemistry. 2013, 322-332

```
                         Enzyme Sequences

LPMO
AA9 LPMO from Podospora anserine (SEQ ID NO: 1).
Genbank ID CAP67740
    1      mkgllsvaal  slavsevsah  yifqqlstgs  tkhgvfqyir  qntnynspvt  dlssndlrcn 61      eggasgantq  tvtvragdsf  tfhldtpvyh  qgpvsvylsk  apgsassydg  sgtwfkikdw 121      gptfpggqwt  lagsytaqlp  scitdgeyll  riqslgihnp  ypagtpqfyi  scaqikvtgg 181      gsvnpsgvai  pgafkatdpg  ytaniysnfn  sytvpgpsvf  scgsngggss  pvepqpqptt 241      tlvtstrapv  atqpagcava  kwgqcggngw  tgcttcaags  tcntqnayyh  qcv
```

Enzyme Sequences

Lichenase
GH16 Lichenase from *Bacillus subtilis* subsp. subtilis str. 168 (SEQ ID NO: 2).
GenBank ID CAA86922.1

```
  1   mpylkrvlll lvtglfmslf avtatasaqt ggsffdpfng ynsgfwqkad gysngnmfnc
 61   twrannvsmt slgemrlalt spaynkfdcg enrsvqtygy glyevrmkpa kntgivssff
121   tytgptdgtp wdeidieflg kdttkvqfny ytngagnhek ivdlgfdaan ayhtyafdwq
181   pnsikwyvdg qlkhtatnqi pttpgkimmn lwngtgvdew lgsyngvnpl yahydwvryt
241   kk
```

Xylanase
GH5 Arabinoxylanase from *Ruminiclostridium thermocellum* (SEQ ID NO: 3).
GenBank ID ABN53395.1

```
  1   mgasiktsik irtvafvsii aialsilsfi pnrayaspqr grprlnaart ffvgdngqpl
 61   rgpytstewt aaapydqiar vkelgfnavh lyaecfdpry papgskapgy avneidkive
121   rtrelglylv itignganng nhnaqwardf wkfyapryak ethvlyeihn epvawgppys
181   sstanppgav dmeidvyrii rtyapetpvl lfsyavfggk ggaaealkdi rafnkavfgn
241   enavwtneav afhgyagwqe ttiaveellk agypcfmtey aggawgsgmg gldvgeltyel
301   erlgvswltf qyipptgvsd dvtkpeyfsa lvensglswt pdygnwpaar gvygngglar
361   etatwinnfl tgttrieaed fdwggngvsy ydtdsvngg qyrpdegvdi ektsdtgggy
421   nvgwisegew leytirvrnp gyynlslrva gisgsrvqvs fgnqdktgvw elpatggfqt
481   wttatrqvfl gaglqklrin alsggfnlnw ielspistgt ipdgtykfln rangktlqev
541   tgnnsiitad ykgiteqhwk iqhigggqyr issagrgwnw nwwmgfgtvg wwgtgsstcf
601   iisptgdgyy rivlvgdgtn lqissgdpsk iegkafhgga nqqwailpvs apafptglsa
661   vldssgntan ltwnaapgan synykrstks ggpyttiatn itstnytdtg vatgtkyyyv
721   vsavsngvet lnsaeailqy pkltgtvigt qgswnnignt ihkafdgdln tffdgptang
781   cwlgldfgeg vrnvitqikf cprsgyeqrm iggifqgank edfsdavtlf titslpgsgt
841   ltsvdvdnpt gfryvrylsp dgsngniael qffgtpagee nddvhlgdin ddgninstdl
901   qmlkrhllrs irltekqlln adtnrdgrvd stdlallkry ilrvittl
```

GH5 Xylanase from *Gonapodya prolifera* (SEQ ID NO: 4).
GenBank ID KXS18720.1

```
  1   marlsslial vlafvavsap alaargrprl ngktfvadsg vplrgpftst ewtpavpaan
 61   ianmrnynfn aihlyaetfd pnypaagsqk pgyaatrvdq ivaatkaanm yvvivlanga
121   nngkfnlnya kdfwsfyaar yknethviye ihnepvqwgp pyisstqspg avsmnadcyk
181   iiravapdtp vllftyasig ggssaagavk daqsfntavf gnanaqwtne aiaihgywga
241   qgasdaakal naagfsvvlt efaaatspts pnggqdtvlt gfmeqggvsw ltflhvpptg
301   vsgdvtdpnq ytnrmtaagi gfdrdpglna vgggqaapvp vpapapvpsp vpapvpavpa
361   vrtttarpap spspvpapvp apapvpapvp apvpapvpap vpapvpaspa atttrrhrtr
421   pprtttapav papppaatpk vcg
```

GH30 xylanase from *Dickeya chiysanthemi* (SEQ ID NO: 5).
GenBank ID AAB53151.1

```
  1   mngnvslwvr hclhaalfvs atagsfsvya dtvkidanvn yqiiqgfggm sgvgwindlt
 61   teqintaygs gvgqiglsim rvridpdssk wniqlpsarq avslgakima tpwsppaymk
121   snnslinggr llpanysayt shlldfskym qtngaplyai siqnepdwkp dyescewsgd
181   efksylksqg skfgslkviv aeslgfnpal tdpvlkdsda skyvsiiggh lygttpkpyp
```

| Enzyme Sequences |
|---|
| 241 laqnagkqlw mtehyvdskq sannwtsaie vgtelnasmv snysayvwwy irrsygllte |
| 301 dgkvskrgyv msqyarfvrp galriqaten pqsnvhltay kntdgkmviv avntndsdqm |
| 361 lslnisnanv tkfekystsa slnveyggss qvdssgkatv wlnplsvttf vsk |
| GH30 xylanase from *Bacillus subtilis* subsp. subtilis str. 168 (SEQ ID NO: 6). GenBank ID CAA97612.1 |
| 1 miprikktic vllvcftmls vmlgpgatev laasdvtvnv saekqvirgf ggmnhpawag |
| 61 dltaaqreta fgngqnqlgf silrihvden rnnwykevet aksavkhgai vfaspwnpps |
| 121 dmvetfnrng dtsakrlkyn kyaayaqhln dfvtfmknng vnlyaisvqn epdyahewtw |
| 181 wtpqeilrfm renagsinar viapesfqyl knlsdpilnd pqalanmdil gthlygtqvs |
| 241 qfpyplfkqk gagkdlwmte vyypnsdtns adrwpealdv sqihnamve gdfqayvwwy |
| 301 irrsygpmke dgtiskrgyn mahfskfvrp gyvridatkn pnanvyvsay kgdnkvviva |
| 361 inksntgvnq nfvlqngsas nvsrwitsss snlqpgtnlt vsgnhfwahl paqsvttfvv |
| 421 nr |
| GH30 Xylanase from *Bacteroides ovatus* (SEQ ID NO: 7). GenBank ID sDY64378.1 |
| 1 mknitllfcl flanillgac sggedekkem degkgayalf lkksitvstg esqtdvvvew |
| 61 aktsweitlg egdivksvtp tsggsntgek qytkvrvscg anstmkkrtq tihlfdktne |
| 121 ttvdllveqe ppfksvtltv dpsvkyqpvv gfggmynpki wcgdnlisas qldkmygagg |
| 181 lgysilrlmi ypnesdwsad veaakaaqan gaiifacpwd ctdaladkit vngkemkhlk |
| 241 kenyeayanh liryvtfmke kgvnlyaisv qnepdmefty wtpsevvdfv kqygariret |
| 301 gvklmspeac gmqpeytdpi innaeafaqt dilaghlyqg ftdlssgyvk nrhdyicgvy |
| 361 sriqgktwwm tehlfndgen sddsskwefl kwqyslnhlg keihmcmegy csayiywylk |
| 421 rfyglmgdtd krsptsegei tkngyimahy aqyatettri kvvtnneevc ataywdektg |
| 481 evtivllnln gasqwleipl agikkasave tnetknmevi dtglmesaeg itvllsansi |
| 541 tsvrltf |
| Xyloglucanase GH5 Xyloglucanase from *Bacteroides ovatus* (SEQ ID NO: 8). GenBank ID ALJ47680.1 |
| 1 mekqsfsdgl fsplgikrvi fmlvllttsf iscsnsdekg gslevaqeyr nlefdargsr |
| 61 qtiqidgpae whistseswc ksshtigegk qyvnitvean dtqkertatv tvsasgapdi |
| 121 iinvkqslys vpaydeyiap dntgmrdlts mqlsalmkag vnvgntfeav ivgndgslsg |
| 181 detcwgnptp nkvlfegika agfdvvripv ayshqfedaa tykiksawmd kveaavkaal |
| 241 daglyviini hweggwlnhp vdankealde rleamwkqia lrfrdyddrl lfagtnevnn |
| 301 ddangaqpte enyrvqngfn qvfvntvrat ggrnhyrhli vqayntdvak avahftmpld |
| 361 ivqnriflec hyydpydfti mpndenfksq wgaafaggdv satgqegdie atlsslnvfi |
| 421 nnnvpviige ygptlrdqlt gealenhlks rndyieyvvk tcvknklvpl ywdagytekl |
| 481 fdrttgqphn aasiaaimkg ln |
| GH8 Xylanase from *Pseudoalteromonas haloplanktis* (SEQ ID NO: 9) PDB: 2A8Z_A |
| 1 afnnnpssvg ayssgtyrnl aqemgktniq qkvnstfdnm fgynnqqly ypytengvyk |
| 61 ahyikainpd egddirtegq swgmtaavml nkqeefdnlw rfakayqknp dnhpdakkqg |
| 121 vyawklklnq ngfvykvdeg papageeyfa fallnasarw gnsgefnyyn daitmlntik |
| 181 nklmenqiir fspyidnltd psyhipafyd yfannvtnqa dknywrqvat ksrtllknhf |

| Enzyme Sequences |
|---|
| 241 tkvsgsphwn lptflsrldg spvigyifng qanpgqwyef dawrvimnvg ldahlmgaqa |
| 301 whksavnkal gflsyaktnn skncyeqvys yggaqnrgca gegqkaanav allastnagq |
| 361 aneffnefws lsqptgdyry yngslymlam lhvsgnfkfy nnffn |
| GH10 Xylanase from *Caldicellulosiruptor owensensis* (SEQ ID NO: 10) GenBank: ADQ03732.1 |
| 1 mseyqdktip slaekykeyf kigaavtvkd legvhgeilv khfnsltpen dmkferihpd |
| 61 ehrynfdavd kmkefaiknn mkmrghtfvw hnqtpewvfk dregndvsre llierlrehi |
| 121 ktvcdryrdi vyawdvvnea vedkteklr dsnwrriigd dyikiafeia keyagegklf |
| 181 yndynnempy klektykllk elidketpid gigiqahwni wdknlidnlk raiemyaslg |
| 241 leiqiteldm svfefedrrt dllepaeemm elqakvyedv fkvfreykgv itsvtfwgis |
| 301 dkhtwkdnfp vigrkdwpll fdvngkpkea ffrivnf |
| GH11 Xylanase from *Thermobifida halotolerans* (SEQ ID NO: 11) GenBank: AEH04392.1 |
| 1 mndapahpks rrhgrirlfv grvctalval vtattmlpgv anaavtsnqt gthdgyfysf |
| 61 wtdspgtvsm elgpggnyst swsntgnfvv gkgwstggrr tvtysgsfnp sgnayltlyg |
| 121 wtrnplveyy ivdnwgtyrp tgtykgtvts dggtydiyet trtnapsieg tatfkqywsv |
| 181 rqsrrtggti tagnhfdawa rhgmnlgshd ymimategyq ssgssnitvg gsgggnpggn |
| 241 pggnpggggc tatlsagqqw sdrynlgvsv sgssnwtvtm nvpspakiia twnisasypn |
| 301 aqtltarpng ngnnwgvtiq hngnwtwptv scsan |

The invention claimed is:

1. A method for producing a sugar substitute, the method comprising:
   (a) contacting, in a solution or suspension, more than one type of polysaccharide-cleaving enzyme and a polysaccharide-containing feedstock to perform one or more enzymatic reactions to provide a reacted feedstock having less than 20% w/w monosaccharides; and
   (b) filtering (i) more than one type of oligosaccharide and (ii) at least one type of monosaccharide from the reacted feedstock of step (a) to produce the sugar substitute, such that the sugar substitute comprises less than 20% w/w monosaccharides and less than 60% w/w disaccharides,
   wherein the more than one type of polysaccharide-cleaving enzyme comprises a xylanase.

2. The method of claim 1, further comprising incorporating the sugar substitute into a foodstuff for human consumption.

3. The method of claim 2, wherein the foodstuff comprises a cake, bread, baked good, chocolate, confectionery, toffee, fudge, meringue, caramel, beverage, dough, cake mixture, or chocolate mixture.

4. The method of claim 1, wherein the sugar substitute has fewer calories per gram than a monosaccharide or disaccharide sugar per gram.

5. The method of claim 4, wherein the monosaccharide and/or disaccharide sugar comprises at least one of glucose, galactose, fructose, maltose, sucrose, or lactose.

6. The method of claim 2, wherein the foodstuff has a comparable texture to a control product comprising only a monosaccharide or disaccharide sugar as a sweetener component.

7. The method of claim 2, wherein the foodstuff has a comparable caramelization property to a control product comprising only a monosaccharide or disaccharide sugar as a sweetener component.

8. The method of claim 1, wherein the sugar substitute has less than 10% w/w monosaccharides.

9. The method of claim 1, wherein the sugar substitute has less than 60% w/w disaccharides.

10. The method of claim 1, wherein the sugar substitute has less than 15% w/w oligosaccharides with 3 residues.

11. The method of claim 1, wherein the sugar substitute has less than 15% w/w oligosaccharides with 4 residues.

12. The method of claim 1, wherein the sugar substitute has less than 15% w/w oligosaccharides with 5 residues.

13. The method of claim 1, wherein the one or more enzymatic reactions produces less than 10% w/w monosaccharides in the solution or suspension.

14. The method of claim 1, wherein the filtered more than one type of oligosaccharide comprises a cello-oligosaccharide having a degree of polymerization (DP) of from two to six.

15. The method of claim 1, wherein the filtered more than one type of oligosaccharide comprises a xylo-oligosaccharide having a degree of polymerization (DP) of from two to twelve.

16. The method of claim 1, wherein the filtered more than one type of oligosaccharide comprises a cello-oligosaccharide having a degree of polymerization (DP) of from two to six and a xylo-oligosaccharide having a degree of polymerization (DP) of from two to twelve.

17. The method of claim 1, wherein the filtered more than one type of oligosaccharide comprises a mixed-linkage glucan-oligosaccharide having a degree of polymerization (DP) of from two to six.

18. The method of claim 1, wherein the filtered at least one type of monosaccharide comprises glucose.

19. The method of claim 1, wherein the filtered at least one type of monosaccharide comprises xylose.

20. The method of claim 1, wherein the filtered at least one type of monosaccharide comprises glucose and xylose.

21. The method of claim 1, wherein the more than one type of polysaccharide-cleaving enzyme is a xylanase.

22. The method of claim 21, wherein the xylanase is at least one of GH5, GH8, GH10, GH11, or GH30 xylanase.

23. The method of claim 1, further comprising pretreating the polysaccharide-containing feedstock with an alkali.

24. The method of claim 1, wherein the filtering in step (b) is ion-exchange chromatography.

25. The method of claim 1, wherein the filtering in step (b) is ultrafiltration.

26. The method of claim 1, wherein the filtering in step (b) is nanofiltration.

27. The method of claim 1, wherein the more than one type of polysaccharide-cleaving enzyme is derived from a fungus or a bacterium.

\* \* \* \* \*

SEQUENCE LISTING

<160> NUMBER OF SEQ ID NOS: 11

<210> SEQ ID NO 1
<211> LENGTH: 293
<212> TYPE: PRT
<213> ORGANISM: Podospora anserina

<400> SEQUENCE: 1

```
Met Lys Gly Leu Leu Ser Val Ala Ala Leu Ser Leu Ala Val Ser Glu
1               5                   10                  15

Val Ser Ala His Tyr Ile Phe Gln Gln Leu Ser Thr Gly Ser Thr Lys
            20                  25                  30

His Gly Val Phe Gln Tyr Ile Arg Gln Asn Thr Asn Tyr Asn Ser Pro
        35                  40                  45

Val Thr Asp Leu Ser Ser Asn Asp Leu Arg Cys Asn Glu Gly Gly Ala
    50                  55                  60

Ser Gly Ala Asn Thr Gln Thr Val Thr Val Arg Ala Gly Asp Ser Phe
65                  70                  75                  80

Thr Phe His Leu Asp Thr Pro Val Tyr His Gln Gly Pro Val Ser Val
                85                  90                  95

Tyr Leu Ser Lys Ala Pro Gly Ser Ala Ser Ser Tyr Asp Gly Ser Gly
            100                 105                 110

Thr Trp Phe Lys Ile Lys Asp Trp Gly Pro Thr Phe Pro Gly Gly Gln
        115                 120                 125

Trp Thr Leu Ala Gly Ser Tyr Thr Ala Gln Leu Pro Ser Cys Ile Thr
    130                 135                 140

Asp Gly Glu Tyr Leu Leu Arg Ile Gln Ser Leu Gly Ile His Asn Pro
```

```
                145                 150                 155                 160
Tyr Pro Ala Gly Thr Pro Gln Phe Tyr Ile Ser Cys Ala Gln Ile Lys
                165                 170                 175
Val Thr Gly Gly Gly Ser Val Asn Pro Ser Gly Val Ala Ile Pro Gly
                180                 185                 190
Ala Phe Lys Ala Thr Asp Pro Gly Tyr Thr Ala Asn Ile Tyr Ser Asn
                195                 200                 205
Phe Asn Ser Tyr Thr Val Pro Gly Pro Ser Val Phe Ser Cys Gly Ser
                210                 215                 220
Asn Gly Gly Gly Ser Ser Pro Val Glu Pro Gln Pro Gln Pro Thr Thr
225                 230                 235                 240
Thr Leu Val Thr Ser Thr Arg Ala Pro Val Ala Thr Gln Pro Ala Gly
                245                 250                 255
Cys Ala Val Ala Lys Trp Gly Gln Cys Gly Gly Asn Gly Trp Thr Gly
                260                 265                 270
Cys Thr Thr Cys Ala Ala Gly Ser Thr Cys Asn Thr Gln Asn Ala Tyr
                275                 280                 285
Tyr His Gln Cys Val
                290

<210> SEQ ID NO 2
<211> LENGTH: 242
<212> TYPE: PRT
<213> ORGANISM: Bacillus subtilis

<400> SEQUENCE: 2

Met Pro Tyr Leu Lys Arg Val Leu Leu Leu Val Thr Gly Leu Phe
1                   5                  10                  15
Met Ser Leu Phe Ala Val Thr Ala Thr Ala Ser Ala Gln Thr Gly Gly
                20                  25                  30
Ser Phe Phe Asp Pro Phe Asn Gly Tyr Asn Ser Gly Phe Trp Gln Lys
                35                  40                  45
Ala Asp Gly Tyr Ser Asn Gly Asn Met Phe Asn Cys Thr Trp Arg Ala
            50                  55                  60
Asn Asn Val Ser Met Thr Ser Leu Gly Glu Met Arg Leu Ala Leu Thr
65                  70                  75                  80
Ser Pro Ala Tyr Asn Lys Phe Asp Cys Gly Glu Asn Arg Ser Val Gln
                85                  90                  95
Thr Tyr Gly Tyr Gly Leu Tyr Glu Val Arg Met Lys Pro Ala Lys Asn
                100                 105                 110
Thr Gly Ile Val Ser Ser Phe Phe Thr Tyr Thr Gly Pro Thr Asp Gly
                115                 120                 125
Thr Pro Trp Asp Glu Ile Asp Ile Glu Phe Leu Gly Lys Asp Thr Thr
            130                 135                 140
Lys Val Gln Phe Asn Tyr Tyr Thr Asn Gly Ala Gly Asn His Glu Lys
145                 150                 155                 160
Ile Val Asp Leu Gly Phe Asp Ala Ala Asn Ala Tyr His Thr Tyr Ala
                165                 170                 175
Phe Asp Trp Gln Pro Asn Ser Ile Lys Trp Tyr Val Asp Gly Gln Leu
                180                 185                 190
Lys His Thr Ala Thr Asn Gln Ile Pro Thr Thr Pro Gly Lys Ile Met
                195                 200                 205
Met Asn Leu Trp Asn Gly Thr Gly Val Asp Glu Trp Leu Gly Ser Tyr
                210                 215                 220
```

-continued

Asn Gly Val Asn Pro Leu Tyr Ala His Tyr Asp Trp Val Arg Tyr Thr
225                 230                 235                 240

Lys Lys

<210> SEQ ID NO 3
<211> LENGTH: 948
<212> TYPE: PRT
<213> ORGANISM: Ruminiclostridium thermocellum

<400> SEQUENCE: 3

Met Gly Ala Ser Ile Lys Thr Ser Ile Lys Ile Arg Thr Val Ala Phe
1               5                   10                  15

Val Ser Ile Ile Ala Ile Ala Leu Ser Ile Leu Ser Phe Ile Pro Asn
                20                  25                  30

Arg Ala Tyr Ala Ser Pro Gln Arg Gly Arg Pro Arg Leu Asn Ala Ala
            35                  40                  45

Arg Thr Thr Phe Val Gly Asp Asn Gly Gln Pro Leu Arg Gly Pro Tyr
        50                  55                  60

Thr Ser Thr Glu Trp Thr Ala Ala Pro Tyr Asp Gln Ile Ala Arg
65                  70                  75                  80

Val Lys Glu Leu Gly Phe Asn Ala Val His Leu Tyr Ala Glu Cys Phe
                85                  90                  95

Asp Pro Arg Tyr Pro Ala Pro Gly Ser Lys Ala Pro Gly Tyr Ala Val
            100                 105                 110

Asn Glu Ile Asp Lys Ile Val Glu Arg Thr Arg Glu Leu Gly Leu Tyr
        115                 120                 125

Leu Val Ile Thr Ile Gly Asn Gly Ala Asn Asn Gly Asn His Asn Ala
    130                 135                 140

Gln Trp Ala Arg Asp Phe Trp Lys Phe Tyr Ala Pro Arg Tyr Ala Lys
145                 150                 155                 160

Glu Thr His Val Leu Tyr Glu Ile His Asn Glu Pro Val Ala Trp Gly
                165                 170                 175

Pro Pro Tyr Ser Ser Ser Thr Ala Asn Pro Pro Gly Ala Val Asp Met
            180                 185                 190

Glu Ile Asp Val Tyr Arg Ile Ile Arg Thr Tyr Ala Pro Glu Thr Pro
        195                 200                 205

Val Leu Leu Phe Ser Tyr Ala Val Phe Gly Lys Gly Gly Ala Ala
    210                 215                 220

Glu Ala Leu Lys Asp Ile Arg Ala Phe Asn Lys Ala Val Phe Gly Asn
225                 230                 235                 240

Glu Asn Ala Val Trp Thr Asn Glu Ala Val Ala Phe His Gly Tyr Ala
                245                 250                 255

Gly Trp Gln Glu Thr Thr Ile Ala Val Glu Glu Leu Leu Lys Ala Gly
            260                 265                 270

Tyr Pro Cys Phe Met Thr Glu Tyr Ala Gly Ala Trp Gly Ser Gly
        275                 280                 285

Met Gly Gly Leu Asp Val Glu Leu Thr Tyr Glu Leu Glu Arg Leu Gly
    290                 295                 300

Val Ser Trp Leu Thr Phe Gln Tyr Ile Pro Thr Gly Val Ser Asp
305                 310                 315                 320

Asp Val Thr Lys Pro Glu Tyr Phe Ser Ala Leu Val Glu Asn Ser Gly
                325                 330                 335

Leu Ser Trp Thr Pro Asp Tyr Gly Asn Trp Pro Ala Ala Arg Gly Val
            340                 345                 350

```
Tyr Gly Asn Gly Gly Leu Ala Arg Glu Thr Ala Thr Trp Ile Asn Asn
            355                 360                 365
Phe Leu Thr Gly Thr Thr Arg Ile Glu Ala Glu Asp Phe Asp Trp Gly
        370                 375                 380
Gly Asn Gly Val Ser Tyr Tyr Asp Thr Asp Ser Val Asn Val Gly Gly
385                 390                 395                 400
Gln Tyr Arg Pro Asp Glu Gly Val Asp Ile Glu Lys Thr Ser Asp Thr
                405                 410                 415
Gly Gly Gly Tyr Asn Val Gly Trp Ile Ser Glu Gly Glu Trp Leu Glu
            420                 425                 430
Tyr Thr Ile Arg Val Arg Asn Pro Gly Tyr Tyr Asn Leu Ser Leu Arg
        435                 440                 445
Val Ala Gly Ile Ser Gly Ser Arg Val Gln Val Ser Phe Gly Asn Gln
    450                 455                 460
Asp Lys Thr Gly Val Trp Glu Leu Pro Ala Thr Gly Phe Gln Thr
465                 470                 475                 480
Trp Thr Thr Ala Thr Arg Gln Val Phe Leu Gly Ala Gly Leu Gln Lys
                485                 490                 495
Leu Arg Ile Asn Ala Leu Ser Gly Gly Phe Asn Leu Asn Trp Ile Glu
            500                 505                 510
Leu Ser Pro Ile Ser Thr Gly Thr Ile Pro Asp Gly Thr Tyr Lys Phe
        515                 520                 525
Leu Asn Arg Ala Asn Gly Lys Thr Leu Gln Glu Val Thr Gly Asn Asn
    530                 535                 540
Ser Ile Ile Thr Ala Asp Tyr Lys Gly Ile Thr Glu Gln His Trp Lys
545                 550                 555                 560
Ile Gln His Ile Gly Gly Gly Gln Tyr Arg Ile Ser Ser Ala Gly Arg
                565                 570                 575
Gly Trp Asn Trp Asn Trp Trp Met Gly Phe Gly Thr Val Gly Trp Trp
            580                 585                 590
Gly Thr Gly Ser Ser Thr Cys Phe Ile Ile Ser Pro Thr Gly Asp Gly
        595                 600                 605
Tyr Tyr Arg Ile Val Leu Val Gly Asp Gly Thr Asn Leu Gln Ile Ser
    610                 615                 620
Ser Gly Asp Pro Ser Lys Ile Glu Gly Lys Ala Phe His Gly Ala
625                 630                 635                 640
Asn Gln Gln Trp Ala Ile Leu Pro Val Ser Ala Pro Ala Phe Pro Thr
                645                 650                 655
Gly Leu Ser Ala Val Leu Asp Ser Ser Gly Asn Thr Ala Asn Leu Thr
            660                 665                 670
Trp Asn Ala Ala Pro Gly Ala Asn Ser Tyr Asn Val Lys Arg Ser Thr
        675                 680                 685
Lys Ser Gly Gly Pro Tyr Thr Thr Ile Ala Thr Asn Ile Thr Ser Thr
    690                 695                 700
Asn Tyr Thr Asp Thr Gly Val Ala Thr Gly Thr Lys Tyr Tyr Tyr Val
705                 710                 715                 720
Val Ser Ala Val Ser Asn Gly Val Glu Thr Leu Asn Ser Ala Glu Ala
                725                 730                 735
Ile Leu Gln Tyr Pro Lys Leu Thr Gly Thr Val Ile Gly Thr Gln Gly
            740                 745                 750
Ser Trp Asn Asn Ile Gly Asn Thr Ile His Lys Ala Phe Asp Gly Asp
        755                 760                 765
Leu Asn Thr Phe Phe Asp Gly Pro Thr Ala Asn Gly Cys Trp Leu Gly
```

```
              770                 775                 780
Leu Asp Phe Gly Glu Gly Val Arg Asn Val Ile Thr Gln Ile Lys Phe
785                 790                 795                 800

Cys Pro Arg Ser Gly Tyr Glu Gln Arg Met Ile Gly Gly Ile Phe Gln
                805                 810                 815

Gly Ala Asn Lys Glu Asp Phe Ser Asp Ala Val Thr Leu Phe Thr Ile
                820                 825                 830

Thr Ser Leu Pro Gly Ser Gly Thr Leu Thr Ser Val Asp Val Asp Asn
                835                 840                 845

Pro Thr Gly Phe Arg Tyr Val Arg Tyr Leu Ser Pro Asp Gly Ser Asn
                850                 855                 860

Gly Asn Ile Ala Glu Leu Gln Phe Phe Gly Thr Pro Ala Gly Glu Glu
865                 870                 875                 880

Asn Asp Asp Val His Leu Gly Asp Ile Asn Asp Asp Gly Asn Ile Asn
                885                 890                 895

Ser Thr Asp Leu Gln Met Leu Lys Arg His Leu Leu Arg Ser Ile Arg
                900                 905                 910

Leu Thr Glu Lys Gln Leu Leu Asn Ala Asp Thr Asn Arg Asp Gly Arg
                915                 920                 925

Val Asp Ser Thr Asp Leu Ala Leu Leu Lys Arg Tyr Ile Leu Arg Val
                930                 935                 940

Ile Thr Thr Leu
945

<210> SEQ ID NO 4
<211> LENGTH: 443
<212> TYPE: PRT
<213> ORGANISM: Gonapodya prolifera

<400> SEQUENCE: 4

Met Ala Arg Leu Ser Ser Leu Ile Ala Leu Val Leu Ala Phe Val Ala
1               5                   10                  15

Val Ser Ala Pro Ala Leu Ala Ala Arg Gly Arg Pro Arg Leu Asn Gly
                20                  25                  30

Lys Thr Phe Val Ala Asp Ser Gly Val Pro Leu Arg Gly Pro Phe Thr
                35                  40                  45

Ser Thr Glu Trp Thr Pro Ala Val Pro Ala Ala Asn Ile Ala Asn Met
                50                  55                  60

Arg Asn Tyr Asn Phe Asn Ala Ile His Leu Tyr Ala Glu Thr Phe Asp
65                  70                  75                  80

Pro Asn Tyr Pro Ala Ala Gly Ser Gln Lys Pro Gly Tyr Ala Ala Thr
                85                  90                  95

Arg Val Asp Gln Ile Val Ala Ala Thr Lys Ala Ala Asn Met Tyr Val
                100                 105                 110

Val Ile Val Leu Ala Asn Gly Ala Asn Asn Gly Lys Phe Asn Leu Asn
                115                 120                 125

Tyr Ala Lys Asp Phe Trp Ser Phe Tyr Ala Ala Arg Tyr Lys Asn Glu
                130                 135                 140

Thr His Val Ile Tyr Glu Ile His Asn Glu Pro Val Gln Trp Gly Pro
145                 150                 155                 160

Pro Tyr Ile Ser Ser Thr Gln Ser Pro Gly Ala Val Ser Met Asn Ala
                165                 170                 175

Asp Cys Tyr Lys Ile Ile Arg Ala Val Ala Pro Asp Thr Pro Val Leu
                180                 185                 190
```

```
Leu Phe Thr Tyr Ala Ser Ile Gly Gly Ser Ser Ala Ala Gly Ala
            195                 200                 205

Val Lys Asp Ala Gln Ser Phe Asn Thr Ala Val Phe Gly Asn Ala Asn
    210                 215                 220

Ala Gln Trp Thr Asn Glu Ala Ile Ala Ile His Gly Tyr Trp Gly Ala
225                 230                 235                 240

Gln Gly Ala Ser Asp Ala Ala Lys Ala Leu Asn Ala Ala Gly Phe Ser
                245                 250                 255

Val Val Leu Thr Glu Phe Ala Ala Thr Ser Pro Thr Ser Pro Asn
            260                 265                 270

Gly Gly Gln Asp Thr Val Leu Thr Gly Phe Met Glu Gln Gln Gly Val
            275                 280                 285

Ser Trp Leu Thr Phe Leu His Val Pro Pro Thr Gly Val Ser Gly Asp
    290                 295                 300

Val Thr Asp Pro Asn Gln Tyr Thr Asn Arg Met Thr Ala Ala Gly Ile
305                 310                 315                 320

Gly Phe Asp Arg Asp Pro Gly Leu Asn Ala Val Gly Gly Gly Gln Ala
                325                 330                 335

Ala Pro Val Pro Val Pro Ala Pro Val Pro Ser Pro Val Pro
            340                 345                 350

Ala Pro Val Pro Ala Val Pro Ala Val Arg Thr Thr Ala Arg Pro
    355                 360                 365

Ala Pro Ser Pro Ser Pro Val Pro Ala Pro Val Pro Ala Pro
370                 375                 380

Val Pro Ala Pro Val Pro Ala Pro Val Pro Ala Pro Val Pro Ala Pro
385                 390                 395                 400

Val Pro Ala Pro Val Pro Ala Ser Pro Ala Thr Thr Arg Arg
                405                 410                 415

His Arg Thr Arg Pro Pro Arg Thr Thr Thr Ala Pro Ala Val Pro Ala
            420                 425                 430

Pro Pro Pro Ala Ala Thr Pro Lys Val Cys Gly
            435                 440

<210> SEQ ID NO 5
<211> LENGTH: 413
<212> TYPE: PRT
<213> ORGANISM: Dickeya chrysanthemi

<400> SEQUENCE: 5

Met Asn Gly Asn Val Ser Leu Trp Val Arg His Cys Leu His Ala Ala
1               5                   10                  15

Leu Phe Val Ser Ala Thr Ala Gly Ser Phe Ser Val Tyr Ala Asp Thr
            20                  25                  30

Val Lys Ile Asp Ala Asn Val Asn Tyr Gln Ile Ile Gln Gly Phe Gly
        35                  40                  45

Gly Met Ser Gly Val Gly Trp Ile Asn Asp Leu Thr Thr Glu Gln Ile
    50                  55                  60

Asn Thr Ala Tyr Gly Ser Gly Val Gly Gln Ile Gly Leu Ser Ile Met
65                  70                  75                  80

Arg Val Arg Ile Asp Pro Asp Ser Ser Lys Trp Asn Ile Gln Leu Pro
                85                  90                  95

Ser Ala Arg Gln Ala Val Ser Leu Gly Ala Lys Ile Met Ala Thr Pro
            100                 105                 110

Trp Ser Pro Pro Ala Tyr Met Lys Ser Asn Asn Ser Leu Ile Asn Gly
        115                 120                 125
```

```
Gly Arg Leu Leu Pro Ala Asn Tyr Ser Ala Tyr Thr Ser His Leu Leu
        130                 135                 140

Asp Phe Ser Lys Tyr Met Gln Thr Asn Gly Ala Pro Leu Tyr Ala Ile
145                 150                 155                 160

Ser Ile Gln Asn Glu Pro Asp Trp Lys Pro Asp Tyr Glu Ser Cys Glu
                165                 170                 175

Trp Ser Gly Asp Glu Phe Lys Ser Tyr Leu Lys Ser Gln Gly Ser Lys
                180                 185                 190

Phe Gly Ser Leu Lys Val Ile Val Ala Glu Ser Leu Gly Phe Asn Pro
                195                 200                 205

Ala Leu Thr Asp Pro Val Leu Lys Asp Ser Asp Ala Ser Lys Tyr Val
        210                 215                 220

Ser Ile Ile Gly Gly His Leu Tyr Gly Thr Thr Pro Lys Pro Tyr Pro
225                 230                 235                 240

Leu Ala Gln Asn Ala Gly Lys Gln Leu Trp Met Thr Glu His Tyr Val
                245                 250                 255

Asp Ser Lys Gln Ser Ala Asn Asn Trp Thr Ser Ala Ile Glu Val Gly
                260                 265                 270

Thr Glu Leu Asn Ala Ser Met Val Ser Asn Tyr Ser Ala Tyr Val Trp
        275                 280                 285

Trp Tyr Ile Arg Arg Ser Tyr Gly Leu Leu Thr Glu Asp Gly Lys Val
        290                 295                 300

Ser Lys Arg Gly Tyr Val Met Ser Gln Tyr Ala Arg Phe Val Arg Pro
305                 310                 315                 320

Gly Ala Leu Arg Ile Gln Ala Thr Glu Asn Pro Gln Ser Asn Val His
                325                 330                 335

Leu Thr Ala Tyr Lys Asn Thr Asp Gly Lys Met Val Ile Val Ala Val
                340                 345                 350

Asn Thr Asn Asp Ser Asp Gln Met Leu Ser Leu Asn Ile Ser Asn Ala
        355                 360                 365

Asn Val Thr Lys Phe Glu Lys Tyr Ser Thr Ser Ala Ser Leu Asn Val
        370                 375                 380

Glu Tyr Gly Gly Ser Ser Gln Val Asp Ser Ser Gly Lys Ala Thr Val
385                 390                 395                 400

Trp Leu Asn Pro Leu Ser Val Thr Thr Phe Val Ser Lys
                405                 410

<210> SEQ ID NO 6
<211> LENGTH: 422
<212> TYPE: PRT
<213> ORGANISM: Bacillus subtilis

<400> SEQUENCE: 6

Met Ile Pro Arg Ile Lys Lys Thr Ile Cys Val Leu Leu Val Cys Phe
1               5                   10                  15

Thr Met Leu Ser Val Met Leu Gly Pro Gly Ala Thr Glu Val Leu Ala
                20                  25                  30

Ala Ser Asp Val Thr Val Asn Val Ser Ala Glu Lys Gln Val Ile Arg
        35                  40                  45

Gly Phe Gly Gly Met Asn His Pro Ala Trp Ala Gly Asp Leu Thr Ala
    50                  55                  60

Ala Gln Arg Glu Thr Ala Phe Gly Asn Gly Gln Asn Gln Leu Gly Phe
65                  70                  75                  80

Ser Ile Leu Arg Ile His Val Asp Glu Asn Arg Asn Asn Trp Tyr Lys
```

```
            85                  90                  95
Glu Val Glu Thr Ala Lys Ser Ala Val Lys His Gly Ala Ile Val Phe
        100                 105                 110

Ala Ser Pro Trp Asn Pro Pro Ser Asp Met Val Glu Thr Phe Asn Arg
        115                 120                 125

Asn Gly Asp Thr Ser Ala Lys Arg Leu Lys Tyr Asn Lys Tyr Ala Ala
        130                 135                 140

Tyr Ala Gln His Leu Asn Asp Phe Val Thr Phe Met Lys Asn Asn Gly
145                 150                 155                 160

Val Asn Leu Tyr Ala Ile Ser Val Gln Asn Glu Pro Asp Tyr Ala His
                165                 170                 175

Glu Trp Thr Trp Trp Thr Pro Gln Glu Ile Leu Arg Phe Met Arg Glu
            180                 185                 190

Asn Ala Gly Ser Ile Asn Ala Arg Val Ile Ala Pro Glu Ser Phe Gln
                195                 200                 205

Tyr Leu Lys Asn Leu Ser Asp Pro Ile Leu Asn Asp Pro Gln Ala Leu
        210                 215                 220

Ala Asn Met Asp Ile Leu Gly Thr His Leu Tyr Gly Thr Gln Val Ser
225                 230                 235                 240

Gln Phe Pro Tyr Pro Leu Phe Lys Gln Lys Gly Ala Gly Lys Asp Leu
                245                 250                 255

Trp Met Thr Glu Val Tyr Tyr Pro Asn Ser Asp Thr Asn Ser Ala Asp
            260                 265                 270

Arg Trp Pro Glu Ala Leu Asp Val Ser Gln His Ile His Asn Ala Met
        275                 280                 285

Val Glu Gly Asp Phe Gln Ala Tyr Val Trp Trp Tyr Ile Arg Arg Ser
        290                 295                 300

Tyr Gly Pro Met Lys Glu Asp Gly Thr Ile Ser Lys Arg Gly Tyr Asn
305                 310                 315                 320

Met Ala His Phe Ser Lys Phe Val Arg Pro Gly Tyr Val Arg Ile Asp
                325                 330                 335

Ala Thr Lys Asn Pro Asn Ala Asn Val Tyr Val Ser Ala Tyr Lys Gly
            340                 345                 350

Asp Asn Lys Val Val Ile Val Ala Ile Asn Lys Ser Asn Thr Gly Val
                355                 360                 365

Asn Gln Asn Phe Val Leu Gln Asn Gly Ser Ala Ser Asn Val Ser Arg
        370                 375                 380

Trp Ile Thr Ser Ser Ser Ser Asn Leu Gln Pro Gly Thr Asn Leu Thr
385                 390                 395                 400

Val Ser Gly Asn His Phe Trp Ala His Leu Pro Ala Gln Ser Val Thr
                405                 410                 415

Thr Phe Val Val Asn Arg
            420

<210> SEQ ID NO 7
<211> LENGTH: 547
<212> TYPE: PRT
<213> ORGANISM: Bacteroides ovatus

<400> SEQUENCE: 7

Met Lys Asn Ile Thr Leu Leu Phe Cys Leu Phe Leu Ala Asn Ile Leu
1               5                   10                  15

Leu Gly Ala Cys Ser Gly Gly Glu Asp Glu Lys Lys Glu Met Asp Glu
            20                  25                  30
```

```
Gly Lys Gly Ala Tyr Ala Leu Phe Leu Lys Lys Ser Ile Thr Val Ser
         35                  40                  45

Thr Gly Glu Ser Gln Thr Asp Val Val Glu Trp Ala Lys Thr Ser
 50                  55                  60

Trp Glu Ile Thr Leu Gly Glu Gly Asp Ile Val Lys Ser Val Thr Pro
 65                  70                  75                  80

Thr Ser Gly Gly Ser Asn Thr Gly Glu Lys Gln Tyr Thr Lys Val Arg
                 85                  90                  95

Val Ser Cys Gly Ala Asn Ser Thr Met Lys Lys Arg Thr Gln Thr Ile
            100                 105                 110

His Leu Phe Asp Lys Thr Asn Glu Thr Thr Val Asp Leu Leu Val Glu
        115                 120                 125

Gln Glu Pro Pro Phe Lys Ser Val Thr Leu Thr Val Asp Pro Ser Val
130                 135                 140

Lys Tyr Gln Pro Val Val Gly Phe Gly Gly Met Tyr Asn Pro Lys Ile
145                 150                 155                 160

Trp Cys Gly Asp Asn Leu Ile Ser Ala Ser Gln Leu Asp Lys Met Tyr
                165                 170                 175

Gly Ala Gly Gly Leu Gly Tyr Ser Ile Leu Arg Leu Met Ile Tyr Pro
            180                 185                 190

Asn Glu Ser Asp Trp Ser Ala Asp Val Glu Ala Ala Lys Ala Ala Gln
        195                 200                 205

Ala Asn Gly Ala Ile Ile Phe Ala Cys Pro Trp Asp Cys Thr Asp Ala
210                 215                 220

Leu Ala Asp Lys Ile Thr Val Asn Gly Lys Glu Met Lys His Leu Lys
225                 230                 235                 240

Lys Glu Asn Tyr Glu Ala Tyr Ala Asn His Leu Ile Arg Tyr Val Thr
                245                 250                 255

Phe Met Lys Glu Lys Gly Val Asn Leu Tyr Ala Ile Ser Val Gln Asn
            260                 265                 270

Glu Pro Asp Met Glu Phe Thr Tyr Trp Thr Pro Ser Glu Val Val Asp
        275                 280                 285

Phe Val Lys Gln Tyr Gly Ala Arg Ile Arg Glu Thr Gly Val Lys Leu
290                 295                 300

Met Ser Pro Glu Ala Cys Gly Met Gln Pro Glu Tyr Thr Asp Pro Ile
305                 310                 315                 320

Ile Asn Asn Ala Glu Ala Phe Ala Gln Thr Asp Ile Leu Ala Gly His
                325                 330                 335

Leu Tyr Gln Gly Phe Thr Asp Leu Ser Ser Gly Tyr Val Lys Asn Arg
            340                 345                 350

His Asp Tyr Ile Cys Gly Val Tyr Ser Arg Ile Gln Gly Lys Thr Trp
        355                 360                 365

Trp Met Thr Glu His Leu Phe Asn Asp Gly Glu Asn Ser Asp Asp Ser
370                 375                 380

Ser Lys Trp Glu Phe Leu Lys Trp Gln Tyr Ser Leu Asn His Leu Gly
385                 390                 395                 400

Lys Glu Ile His Met Cys Met Glu Gly Tyr Cys Ser Ala Tyr Ile Tyr
                405                 410                 415

Trp Tyr Leu Lys Arg Phe Tyr Gly Leu Met Gly Asp Thr Asp Lys Arg
            420                 425                 430

Ser Pro Thr Ser Glu Gly Glu Ile Thr Lys Asn Gly Tyr Ile Met Ala
        435                 440                 445

His Tyr Ala Gln Tyr Ala Thr Glu Thr Thr Arg Ile Lys Val Val Thr
```

```
                450             455             460
Asn Asn Glu Glu Val Cys Ala Thr Ala Tyr Trp Asp Glu Lys Thr Gly
465                 470                 475                 480

Glu Val Thr Ile Val Leu Leu Asn Leu Asn Gly Ala Ser Gln Trp Leu
                    485                 490                 495

Glu Ile Pro Leu Ala Gly Ile Lys Lys Ala Ser Ala Val Glu Thr Asn
                500                 505                 510

Glu Thr Lys Asn Met Glu Val Ile Asp Thr Gly Leu Met Glu Ser Ala
            515                 520                 525

Glu Gly Ile Thr Val Leu Leu Ser Ala Asn Ser Ile Thr Ser Val Arg
        530                 535                 540

Leu Thr Phe
545

<210> SEQ ID NO 8
<211> LENGTH: 502
<212> TYPE: PRT
<213> ORGANISM: Bacteroides ovatus

<400> SEQUENCE: 8

Met Glu Lys Gln Ser Phe Ser Asp Gly Leu Phe Ser Pro Leu Gly Ile
1               5                   10                  15

Lys Arg Val Ile Phe Met Leu Val Leu Leu Thr Thr Ser Phe Ile Ser
            20                  25                  30

Cys Ser Asn Ser Asp Glu Lys Gly Gly Ser Leu Glu Val Ala Gln Glu
        35                  40                  45

Tyr Arg Asn Leu Glu Phe Asp Ala Arg Gly Ser Arg Gln Thr Ile Gln
    50                  55                  60

Ile Asp Gly Pro Ala Glu Trp His Ile Ser Thr Ser Glu Ser Trp Cys
65                  70                  75                  80

Lys Ser Ser His Thr Ile Gly Glu Gly Lys Gln Tyr Val Asn Ile Thr
                85                  90                  95

Val Glu Ala Asn Asp Thr Gln Lys Glu Arg Thr Ala Thr Val Thr Val
            100                 105                 110

Ser Ala Ser Gly Ala Pro Asp Ile Ile Ile Asn Val Lys Gln Ser Leu
        115                 120                 125

Tyr Ser Val Pro Ala Tyr Asp Glu Tyr Ile Ala Pro Asp Asn Thr Gly
    130                 135                 140

Met Arg Asp Leu Thr Ser Met Gln Leu Ser Ala Leu Met Lys Ala Gly
145                 150                 155                 160

Val Asn Val Gly Asn Thr Phe Glu Ala Val Ile Val Gly Asn Asp Gly
                165                 170                 175

Ser Leu Ser Gly Asp Glu Thr Cys Trp Gly Asn Pro Thr Pro Asn Lys
            180                 185                 190

Val Leu Phe Glu Gly Ile Lys Ala Ala Gly Phe Asp Val Val Arg Ile
        195                 200                 205

Pro Val Ala Tyr Ser His Gln Phe Glu Asp Ala Ala Thr Tyr Lys Ile
    210                 215                 220

Lys Ser Ala Trp Met Asp Lys Val Glu Ala Ala Val Lys Ala Ala Leu
225                 230                 235                 240

Asp Ala Gly Leu Tyr Val Ile Ile Asn Ile His Trp Glu Gly Gly Trp
                245                 250                 255

Leu Asn His Pro Val Asp Ala Asn Lys Glu Ala Leu Asp Glu Arg Leu
            260                 265                 270
```

```
Glu Ala Met Trp Lys Gln Ile Ala Leu Arg Phe Arg Asp Tyr Asp Asp
            275                 280                 285

Arg Leu Leu Phe Ala Gly Thr Asn Glu Val Asn Asn Asp Asp Ala Asn
        290                 295                 300

Gly Ala Gln Pro Thr Glu Glu Asn Tyr Arg Val Gln Asn Gly Phe Asn
305                 310                 315                 320

Gln Val Phe Val Asn Thr Val Arg Ala Thr Gly Gly Arg Asn His Tyr
                325                 330                 335

Arg His Leu Ile Val Gln Ala Tyr Asn Thr Asp Val Ala Lys Ala Val
            340                 345                 350

Ala His Phe Thr Met Pro Leu Asp Ile Val Gln Asn Arg Ile Phe Leu
        355                 360                 365

Glu Cys His Tyr Tyr Asp Pro Tyr Asp Phe Thr Ile Met Pro Asn Asp
370                 375                 380

Glu Asn Phe Lys Ser Gln Trp Gly Ala Ala Phe Ala Gly Gly Asp Val
385                 390                 395                 400

Ser Ala Thr Gly Gln Glu Gly Asp Ile Glu Ala Thr Leu Ser Ser Leu
                405                 410                 415

Asn Val Phe Ile Asn Asn Asn Val Pro Val Ile Ile Gly Glu Tyr Gly
            420                 425                 430

Pro Thr Leu Arg Asp Gln Leu Thr Gly Glu Ala Leu Glu Asn His Leu
        435                 440                 445

Lys Ser Arg Asn Asp Tyr Ile Glu Tyr Val Val Lys Thr Cys Val Lys
    450                 455                 460

Asn Lys Leu Val Pro Leu Tyr Trp Asp Ala Gly Tyr Thr Glu Lys Leu
465                 470                 475                 480

Phe Asp Arg Thr Thr Gly Gln Pro His Asn Ala Ala Ser Ile Ala Ala
                485                 490                 495

Ile Met Lys Gly Leu Asn
            500

<210> SEQ ID NO 9
<211> LENGTH: 405
<212> TYPE: PRT
<213> ORGANISM: Pseudoalteromonas haloplanktis

<400> SEQUENCE: 9

Ala Phe Asn Asn Asn Pro Ser Ser Val Gly Ala Tyr Ser Ser Gly Thr
1               5                   10                  15

Tyr Arg Asn Leu Ala Gln Glu Met Gly Lys Thr Asn Ile Gln Gln Lys
            20                  25                  30

Val Asn Ser Thr Phe Asp Asn Met Phe Gly Tyr Asn Asn Thr Gln Gln
        35                  40                  45

Leu Tyr Tyr Pro Tyr Thr Glu Asn Gly Val Tyr Lys Ala His Tyr Ile
    50                  55                  60

Lys Ala Ile Asn Pro Asp Glu Gly Asp Ile Arg Thr Glu Gly Gln
65                  70                  75                  80

Ser Trp Gly Met Thr Ala Ala Val Met Leu Asn Lys Gln Glu Glu Phe
                85                  90                  95

Asp Asn Leu Trp Arg Phe Ala Lys Ala Tyr Gln Lys Asn Pro Asp Asn
            100                 105                 110

His Pro Asp Ala Lys Lys Gln Gly Val Tyr Ala Trp Lys Leu Lys Leu
        115                 120                 125

Asn Gln Asn Gly Phe Val Tyr Lys Val Asp Glu Gly Pro Ala Pro Ala
    130                 135                 140
```

Gly Glu Glu Tyr Phe Ala Phe Ala Leu Leu Asn Ala Ser Ala Arg Trp
145                 150                 155                 160

Gly Asn Ser Gly Glu Phe Asn Tyr Tyr Asn Asp Ala Ile Thr Met Leu
            165                 170                 175

Asn Thr Ile Lys Asn Lys Leu Met Glu Asn Gln Ile Ile Arg Phe Ser
            180                 185                 190

Pro Tyr Ile Asp Asn Leu Thr Asp Pro Ser Tyr His Ile Pro Ala Phe
            195                 200                 205

Tyr Asp Tyr Phe Ala Asn Asn Val Thr Asn Gln Ala Asp Lys Asn Tyr
            210                 215                 220

Trp Arg Gln Val Ala Thr Lys Ser Arg Thr Leu Leu Lys Asn His Phe
225                 230                 235                 240

Thr Lys Val Ser Gly Ser Pro His Trp Asn Leu Pro Thr Phe Leu Ser
            245                 250                 255

Arg Leu Asp Gly Ser Pro Val Ile Gly Tyr Ile Phe Asn Gly Gln Ala
            260                 265                 270

Asn Pro Gly Gln Trp Tyr Glu Phe Asp Ala Trp Arg Val Ile Met Asn
            275                 280                 285

Val Gly Leu Asp Ala His Leu Met Gly Ala Gln Ala Trp His Lys Ser
            290                 295                 300

Ala Val Asn Lys Ala Leu Gly Phe Leu Ser Tyr Ala Lys Thr Asn Asn
305                 310                 315                 320

Ser Lys Asn Cys Tyr Glu Gln Val Tyr Ser Tyr Gly Gly Ala Gln Asn
            325                 330                 335

Arg Gly Cys Ala Gly Glu Gly Gln Lys Ala Ala Asn Ala Val Ala Leu
            340                 345                 350

Leu Ala Ser Thr Asn Ala Gly Gln Ala Asn Glu Phe Phe Asn Glu Phe
            355                 360                 365

Trp Ser Leu Ser Gln Pro Thr Gly Asp Tyr Arg Tyr Tyr Asn Gly Ser
            370                 375                 380

Leu Tyr Met Leu Ala Met Leu His Val Ser Gly Asn Phe Lys Phe Tyr
385                 390                 395                 400

Asn Asn Thr Phe Asn
            405

<210> SEQ ID NO 10
<211> LENGTH: 337
<212> TYPE: PRT
<213> ORGANISM: Caldicellulosiruptor owensensis

<400> SEQUENCE: 10

Met Ser Glu Tyr Gln Asp Lys Thr Ile Pro Ser Leu Ala Glu Lys Tyr
1               5                   10                  15

Lys Glu Tyr Phe Lys Ile Gly Ala Ala Val Thr Val Lys Asp Leu Glu
                20                  25                  30

Gly Val His Gly Glu Ile Leu Val Lys His Phe Asn Ser Leu Thr Pro
            35                  40                  45

Glu Asn Asp Met Lys Phe Glu Arg Ile His Pro Asp Glu His Arg Tyr
        50                  55                  60

Asn Phe Asp Ala Val Asp Lys Met Lys Glu Phe Ala Ile Lys Asn Asn
65                  70                  75                  80

Met Lys Met Arg Gly His Thr Phe Val Trp His Asn Gln Thr Pro Glu
                85                  90                  95

Trp Val Phe Lys Asp Arg Glu Gly Asn Asp Val Ser Arg Glu Leu Leu

```
                100             105             110
Ile Glu Arg Leu Arg Glu His Ile Lys Thr Val Cys Asp Arg Tyr Arg
            115                 120                 125

Asp Ile Val Tyr Ala Trp Asp Val Val Asn Glu Ala Val Glu Asp Lys
        130                 135                 140

Thr Glu Lys Leu Leu Arg Asp Ser Asn Trp Arg Arg Ile Ile Gly Asp
145                 150                 155                 160

Asp Tyr Ile Lys Ile Ala Phe Glu Ile Ala Lys Glu Tyr Ala Gly Glu
                165                 170                 175

Gly Lys Leu Phe Tyr Asn Asp Tyr Asn Asn Glu Met Pro Tyr Lys Leu
            180                 185                 190

Glu Lys Thr Tyr Lys Leu Leu Lys Glu Leu Ile Asp Lys Glu Thr Pro
        195                 200                 205

Ile Asp Gly Ile Gly Ile Gln Ala His Trp Asn Ile Trp Asp Lys Asn
    210                 215                 220

Leu Ile Asp Asn Leu Lys Arg Ala Ile Glu Met Tyr Ala Ser Leu Gly
225                 230                 235                 240

Leu Glu Ile Gln Ile Thr Glu Leu Asp Met Ser Val Phe Glu Phe Glu
                245                 250                 255

Asp Arg Arg Thr Asp Leu Leu Glu Pro Ala Glu Met Met Glu Leu
            260                 265                 270

Gln Ala Lys Val Tyr Glu Asp Val Phe Lys Val Phe Arg Glu Tyr Lys
        275                 280                 285

Gly Val Ile Thr Ser Val Thr Phe Trp Gly Ile Ser Asp Lys His Thr
    290                 295                 300

Trp Lys Asp Asn Phe Pro Val Ile Gly Arg Lys Asp Trp Pro Leu Leu
305                 310                 315                 320

Phe Asp Val Asn Gly Lys Pro Lys Glu Ala Phe Phe Arg Ile Val Asn
                325                 330                 335

Phe

<210> SEQ ID NO 11
<211> LENGTH: 335
<212> TYPE: PRT
<213> ORGANISM: Thermobifida halotolerans

<400> SEQUENCE: 11

Met Asn Asp Ala Pro Ala His Pro Lys Ser Arg Arg His Gly Arg Ile
1               5                   10                  15

Arg Leu Phe Val Gly Arg Val Cys Thr Ala Leu Val Ala Leu Val Thr
            20                  25                  30

Ala Thr Thr Met Leu Pro Gly Val Ala Asn Ala Ala Val Thr Ser Asn
        35                  40                  45

Gln Thr Gly Thr His Asp Gly Tyr Phe Tyr Ser Phe Trp Thr Asp Ser
    50                  55                  60

Pro Gly Thr Val Ser Met Glu Leu Gly Pro Gly Gly Asn Tyr Ser Thr
65                  70                  75                  80

Ser Trp Ser Asn Thr Gly Asn Phe Val Val Gly Lys Gly Trp Ser Thr
                85                  90                  95

Gly Gly Arg Arg Thr Val Thr Tyr Ser Gly Ser Phe Asn Pro Ser Gly
            100                 105                 110

Asn Ala Tyr Leu Thr Leu Tyr Gly Trp Thr Arg Asn Pro Leu Val Glu
        115                 120                 125

Tyr Tyr Ile Val Asp Asn Trp Gly Thr Tyr Arg Pro Thr Gly Thr Tyr
```

-continued

```
            130                 135                 140
Lys Gly Thr Val Thr Ser Asp Gly Gly Thr Tyr Asp Ile Tyr Glu Thr
145                 150                 155                 160

Thr Arg Thr Asn Ala Pro Ser Ile Glu Gly Thr Ala Thr Phe Lys Gln
                165                 170                 175

Tyr Trp Ser Val Arg Gln Ser Arg Arg Thr Gly Gly Thr Ile Thr Ala
                180                 185                 190

Gly Asn His Phe Asp Ala Trp Ala Arg His Gly Met Asn Leu Gly Ser
            195                 200                 205

His Asp Tyr Met Ile Met Ala Thr Glu Gly Tyr Gln Ser Ser Gly Ser
        210                 215                 220

Ser Asn Ile Thr Val Gly Gly Ser Gly Gly Gly Asn Pro Gly Gly Asn
225                 230                 235                 240

Pro Gly Gly Asn Pro Gly Gly Gly Gly Cys Thr Ala Thr Leu Ser Ala
                245                 250                 255

Gly Gln Gln Trp Ser Asp Arg Tyr Asn Leu Gly Val Ser Val Ser Gly
                260                 265                 270

Ser Ser Asn Trp Thr Val Thr Met Asn Val Pro Ser Pro Ala Lys Ile
            275                 280                 285

Ile Ala Thr Trp Asn Ile Ser Ala Ser Tyr Pro Asn Ala Gln Thr Leu
        290                 295                 300

Thr Ala Arg Pro Asn Gly Asn Gly Asn Asn Trp Gly Val Thr Ile Gln
305                 310                 315                 320

His Asn Gly Asn Trp Thr Trp Pro Thr Val Ser Cys Ser Ala Asn
                325                 330                 335
```